US012611228B2

(12) United States Patent
Bell et al.

(10) Patent No.: US 12,611,228 B2
(45) Date of Patent: Apr. 28, 2026

(54) DETACHABLE GEARED-MOTOR ASSEMBLY FOR MOTORIZING A STRUT IN A SPATIAL FRAME

(71) Applicants:Smith & Nephew, Inc., Memphis, TN (US); Smith & Nephew Orthopaedics AG, Zug (CH); Smith & Nephew Asia Pacific PTE. Limited, Singapore (SG)

(72) Inventors: Paul Bell, Memphis, TN (US); Sied Janna, Memphis, TN (US); Darren J. Wilson, Hull (GB); Andrew P. Noblett, Bartlett, TN (US); Brian Roberts, Germantown, TN (US); Johnny R. Mason, Bartlett, TN (US); Scott Smyth, Memphis, TN (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 12 days.

(21) Appl. No.: 18/839,091

(22) PCT Filed: Feb. 14, 2023

(86) PCT No.: PCT/US2023/013011
§ 371 (c)(1),
(2) Date: Aug. 16, 2024

(87) PCT Pub. No.: WO2023/163874
PCT Pub. Date: Aug. 31, 2023

(65) Prior Publication Data
US 2025/0177005 A1 Jun. 5, 2025

Related U.S. Application Data

(60) Provisional application No. 63/312,760, filed on Feb. 22, 2022.

(51) Int. Cl.
A61B 17/64 (2006.01)
A61B 17/00 (2006.01)
A61B 17/66 (2006.01)

(52) U.S. Cl.
CPC ............ *A61B 17/645* (2013.01); *A61B 17/66* (2013.01); *A61B 2017/00221* (2013.01); *A61B 2017/00398* (2013.01)

(58) Field of Classification Search
CPC .................. A61B 17/645; A61B 17/66; A61B 2017/00221; A61B 2017/00398
See application file for complete search history.

(56) References Cited

U.S. PATENT DOCUMENTS

| | | | |
|---|---|---|---|
| 5,702,389 A | 12/1997 | Taylor et al. | |
| 5,728,095 A | 3/1998 | Taylor et al. | |
| (Continued) | | | |

FOREIGN PATENT DOCUMENTS

| | | |
|---|---|---|
| CN | 106264690 A | 1/2017 |
| DE | 10151754 A1 | 5/2003 |
| (Continued) | | |

OTHER PUBLICATIONS

Wendlandt Robert et al., "Bone mounted hexapod robot for outpatient distraction osteogenesis", 4th European Conference of the International Federation for Medical and Biological Engineering, 2009, vol. 22, 2009, pp. 1679-1682.

(Continued)

*Primary Examiner* — Nicholas J Plionis
(74) *Attorney, Agent, or Firm* — KDW Firm PLLC

(57) ABSTRACT

A geared-motor assembly for use in a spatial frame is disclosed. Each of the geared-motor assemblies being selectively attachable and detachable from a manually adjustable strut in a spatial frame. In use, with the geared-motor assemblies detached, the struts can be manually adjusted (Continued)

(e.g., rotated) to, for example, facilitate initial construction of the spatial frame in the operating room, to allow patients to manually adjust the struts if desired, etc. Thereafter, with the geared-motor assemblies coupled to the struts, motorized and/or automated adjustment of the struts according to a treatment plan can be achieved. In use, each of the geared-motor assemblies is configured as a stand-alone device including all of the needed intelligence (e.g., microprocessor, printed-circuit board, etc.) and power supply to control and power the geared-motor assembly so that no external wires or centralized controller is required.

23 Claims, 23 Drawing Sheets

(56)     References Cited

U.S. PATENT DOCUMENTS

| | | | |
|---|---|---|---|
| 5,891,143 | A | 4/1999 | Taylor et al. |
| 5,971,984 | A | 10/1999 | Taylor et al. |
| 6,030,386 | A | 2/2000 | Taylor et al. |
| 6,129,727 | A | 10/2000 | Austin et al. |
| RE40,914 | E | 9/2009 | Taylor et al. |
| 2002/0010465 | A1 | 1/2002 | Koo et al. |
| 2003/0191466 | A1 | 10/2003 | Austin et al. |
| 2004/0073211 | A1 | 4/2004 | Austin et al. |
| 2005/0215997 | A1 | 9/2005 | Austin et al. |
| 2011/0004199 | A1* | 1/2011 | Ross .................... A61B 90/98 606/1 |
| 2016/0092651 | A1 | 3/2016 | Austin et al. |
| 2021/0038147 | A1 | 2/2021 | Cohen et al. |
| 2023/0277220 | A1* | 9/2023 | Harari ................... A61B 17/62 606/56 |

FOREIGN PATENT DOCUMENTS

| | | | |
|---|---|---|---|
| WO | 2009105479 | A1 | 8/2009 |
| WO | 2021061816 | A1 | 4/2021 |
| WO | 2022024133 | A1 | 2/2022 |

OTHER PUBLICATIONS

International Search Report and Written Opinion for International Application No. PCT/US2023/013011, filed on Feb. 14, 2023, 14 pages.

* cited by examiner

100

102

106-1

106-4

106-5

106-2

106-6

106-3

104

410, 415

419

418

417

416

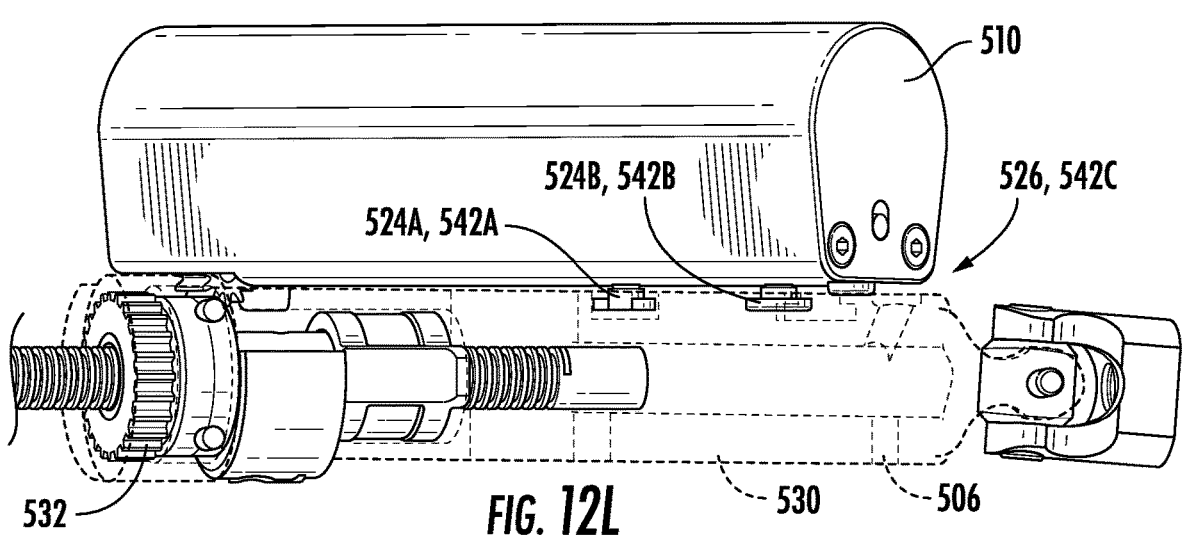
524B, 542B
524A, 542A
526, 542C
532
*FIG.* 12L
530
506
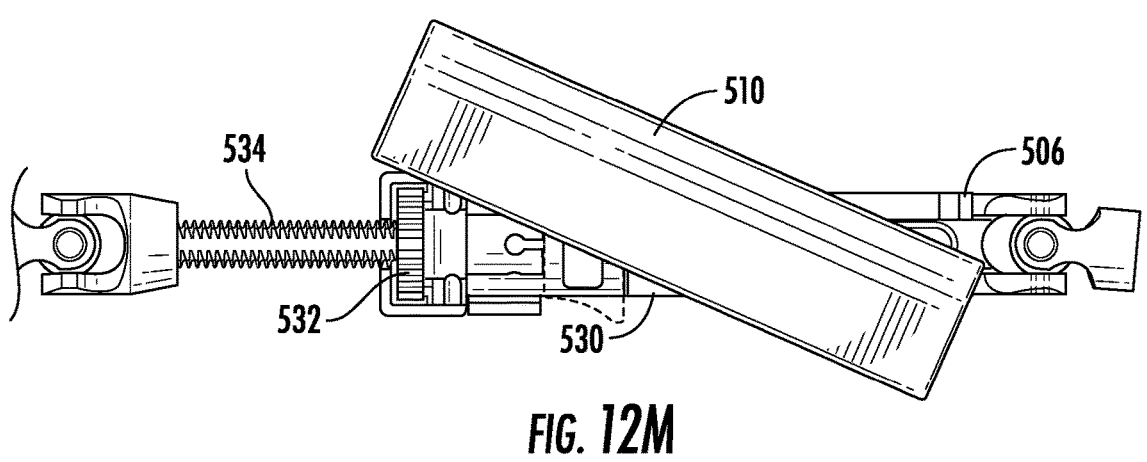
534
510
506
532
530
*FIG.* 12M

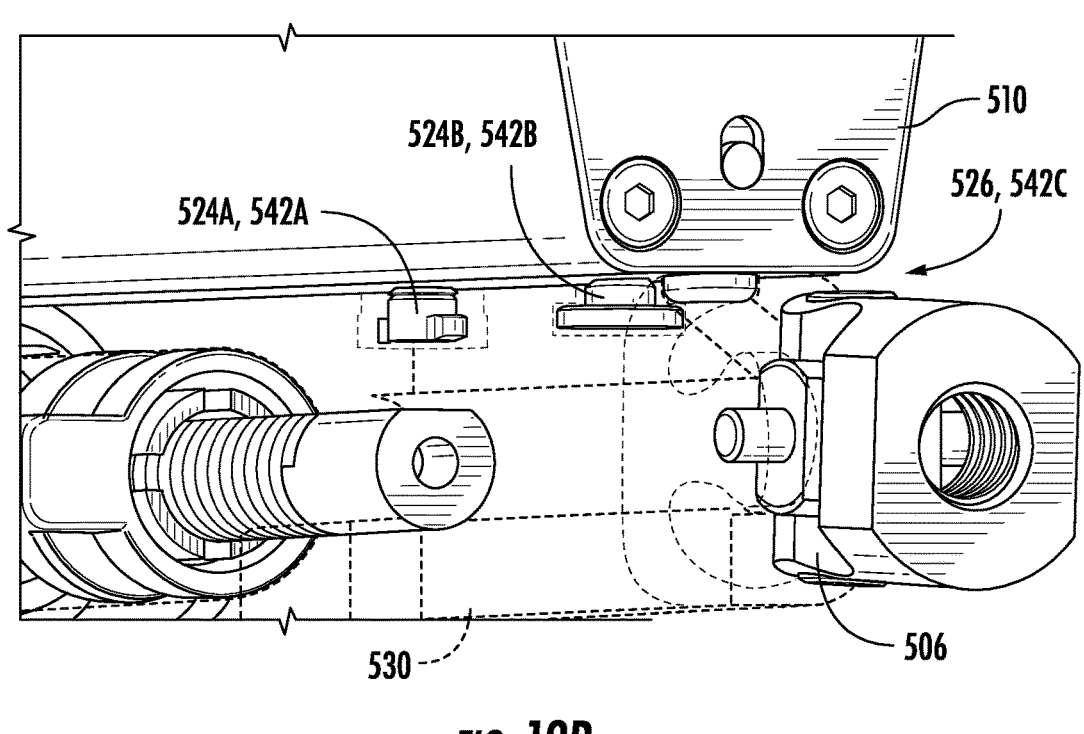
FIG. *12P*
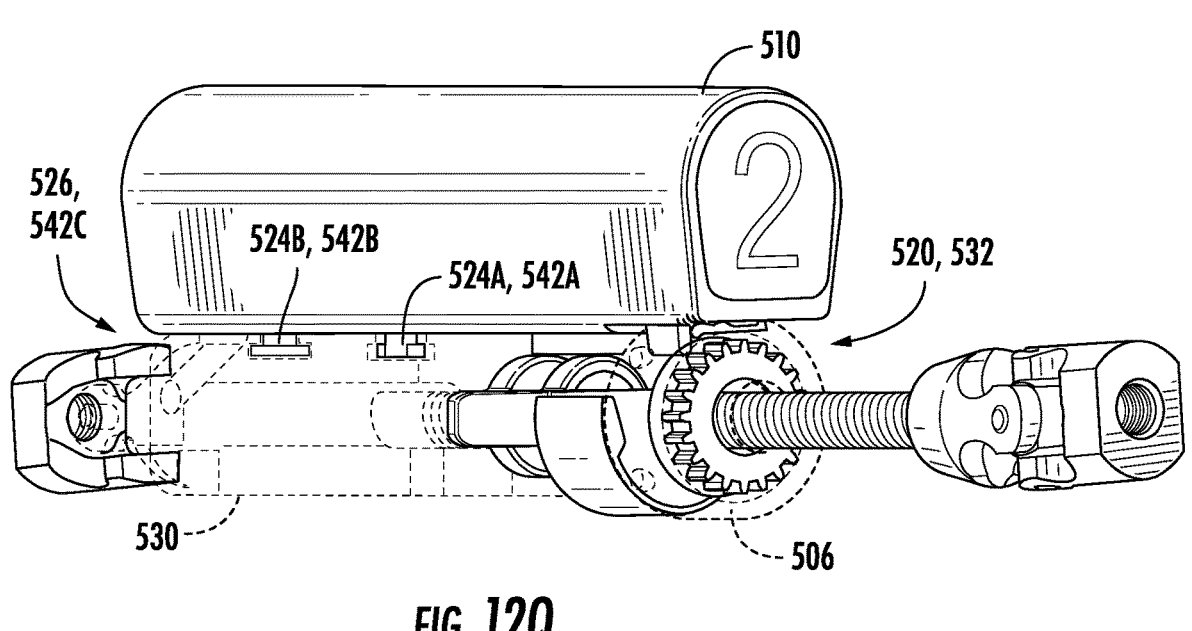
FIG. *12Q*

DETACHABLE GEARED-MOTOR ASSEMBLY FOR MOTORIZING A STRUT IN A SPATIAL FRAME

CROSS-REFERENCE TO RELATED APPLICATIONS

This application is a National Phase filing of International Application No. PCT/US2023/013011, filed Feb. 14, 2023, which application is a non-provisional of, and claims the benefit of the filing date of, U.S. provisional patent application No. 63/312,760, filed Feb. 22, 2022, entitled "Detachable Geared-Motor Assembly for Motorizing a Strut in a Spatial Frame," the entirety of each application is incorporated by reference herein.

FIELD OF THE DISCLOSURE

The present disclosure relates generally to orthopedic devices, systems, and methods for facilitating fracture alignment such as the treatment of musculoskeletal conditions with a spatial frame, and particularly to a geared-motor assembly selectively attached and detached from a manually adjustable strut. In use, with the geared-motor assembly detached, the struts can be manually adjusted (e.g., rotated) to, for example, facilitate initial construction of the spatial frame in the operating room, to allow patients to manually adjust the struts if desired, etc. Thereafter, with the geared-motor assemblies coupled to the struts, motorized and/or automated adjustment of the struts according to a treatment plan can be achieved.

BACKGROUND OF THE DISCLOSURE

People suffer bone fractures each year. In many instances, a person that suffers a bone fracture is required to use a bone alignment device, an external fixation system, etc. such as, for example, a spatial frame, a hexapod, etc. (terms used interchangeably herein without the intent to limit or distinguish) to align two or more bones, bone fragments, bone pieces, etc. (terms used interchangeably herein without the intent to limit or distinguish). Generally speaking, spatial frames allow for polyaxial movement of the coupled bones and are typically used to keep fractured bones stabilized and in alignment during a treatment period.

Generally speaking, the spatial frame includes first and second rings, platforms, frames, bases, etc. (terms used interchangeably herein without the intent to limit or distinguish) intercoupled by a plurality of struts. In use, the struts have adjustable lengths that may be manually adjusted regularly (e.g., daily) in accordance with a prescription or treatment plan (terms used interchangeably herein without the intent to limit or distinguish). As the lengths of the struts are adjusted, the platforms may be brought closer together or moved farther apart. The treatment plan specifies strut length adjustments to be made to each of the struts over time to ensure successful bone alignment.

One known example of a spatial frame is the TAYLOR SPATIAL FRAME® manufactured and sold by Smith Nephew, Inc. The TAYLOR SPATIAL FRAME® is based on the general concept of a Stewart platform. Smith & Nephew, Inc. is the owner of U.S. Pat. Nos. 5,702,389; 5,728,095; 5,891,143; RE40,914, 5,971,984; 6,030,386; and 6,129,727; and U.S. Published patents application Nos. 20030191466; 2004/0073211; 2005/0215997; and 2016/0092651 that disclose many concepts of and improvements to the Stewart platform based spatial frame, including methods of use, systems, and devices that enhance use of the spatial frame.

Referring to FIG. 1 one known example of a spatial frame 100 is illustrated. As shown in FIG. 1, the spatial frame 100 may form a hexapod having a circular, metal frame with a first platform 102 and a second platform 104 connected by six adjustable length struts 106 (labeled as struts 106-1 through 106-6 in FIG. 1). Each strut 106 may be independently lengthened or shortened relative to the rest of the frame, thereby allowing for six different axes of movement.

Each strut 106 may include an outer body and an inner body, which may be configured as, or be operatively coupled to, a threaded rod (also referred to as a lead screw). The outer body may be coupled to one of the platforms, such as, the second platform 104 by way of a joint as shown. The inner body may be coupled to the other platform, such as, the first platform 102 by way of a joint as shown. To lengthen or shorten one of struts 106, the outer body and the inner body may be moved or translated relative to one another. For example, the strut 106 may include an adjustment nut wherein rotation of the adjustment nut moves the inner body (e.g., threaded rod or lead screw) relative to the outer body to adjust an overall length of the strut.

In use, the spatial frame 100 may be used to treat a variety of skeletal fractures of a patient. Typically, the spatial frame 100 is positioned around the patient and is used to align two or more bone portions. To do so, a length of each strut 106 may be incrementally adjusted (e.g., shortened or lengthened) in accordance with a treatment plan that specifies adjustments to be made to each strut 106 over time to ensure successful bone alignment. In many instances, the length of each strut 106 should be adjusted daily to comply with the provided treatment plan. Adjusting the length of each strut 106 adjusts the distance and/or position between the first and second platforms 102, 104, and hence the first and second bone portions coupled thereto.

During use, patient's bones are normally adjusted (e.g., lengthened, shortened, etc.) manually, for example, by hand or a wrench at a rate of approximately 1 mm/day, which is then proceeded by a consolidation phase before the spatial frame is removed.

It is theoretically known in the prior art to automate and/or motorize adjustment of a spatial frame by motorizing or otherwise automating strut adjustments. For example, one known motorized strut is the Robotic Hexapod System manufactured by Orthospin Ltd. In use, the Robotic Hexapod System includes an offset motor design that engages custom struts positioned between the first and second platforms. That is, the motor includes a spur gear engaged with a second spur gear associated with the threaded rod of the strut. In use, rotation from the motor drives rotation of the threaded rod via the interaction between the spur gears. The Robotic Hexapod System however suffers from a number of disadvantages including being very bulky and having trailing cables.

However, currently commercially available spatial frames are dependent on manual adjustment of each strut. As a result of the requirement for manual adjustments, generally speaking, successful treatment requires patient compliance (e.g., daily manual adjustments to each of the struts) to avoid human error. In routine clinical practice, the treatment plan may require multiple daily adjustments to be made to each of the plurality of struts. For example, a patient may be required to manually adjust one or more of the struts, typically two or more times each day, and often over long periods of time with support from either a family member, a clinician, or both. As such, compliance with the treatment plan may be burdensome, painful, and prone to errors, which may rise as the number of manual daily adjustment increases.

As a result, the number of adjustments dictated by the treatment plan may be limited. For example, generally speaking, treatment plans often limit the required number of daily adjustments to each of the plurality of struts to four per day. During a normal treatment plan, this may equate to approximately 720 adjustments (e.g., turns) over a one-month treatment span (e.g., 6 struts×4 adjustments per day×30 days). During an extended treatment plan for more severe applications, this may equate to approximately 2,160 adjustments (e.g., turns) over a three-month treatment span (e.g., 6 struts×4 adjustments per day×90 days).

In addition, during the treatment period, the patient may require numerous clinical visits to confirm proper strut adjustments to ensure compliance and avoid incorrect adjustment, which has historically been the leading cause of treatment failure.

Motorized and/or automated spatial frames could provide numerous advantages over manually adjustable struts. In use, electric motors, motor-drive units, and a control unit (e.g., a central control unit) could function to supersede the manual actuation of the strut adjustments. For example, an automated and/or motorized system could eliminate the need for patient compliance and decrease the frequency of post-operative visits for patient supervision given that the spatial frame may only need to be activated at the start of the distraction phase and terminated at the end of the distraction phase without any patient intervention. As a result, the burden of manual adjustment can be overcome by automating and/or motorizing the struts, which in turn, enables a more independent lifestyle during treatment.

In addition, as a programmable multi-purpose device, automated and/or motorized spatial frames allow the implementation of more diverse treatment schedules. For example, automatic and/or motorized distraction could enable a higher distraction frequency and result in smaller excursions per activation. Smaller excursions or adjustments have the potential to result in less damage to the distracted tissues, improving bone regeneration and adaptation of the surrounding soft tissues. That is, spatial frames equipped with motorized and/or automated struts offer the potential to increase the number of daily distraction adjustments by enabling finer (e.g., smaller) adjustments at a controllable rate and frequency of distraction that encourages better quality bone formation. Making finer (e.g., smaller) adjustments during limb lengthening can have significant advantages in terms of reduced soft tissue damage, less pain, and opioid usage and accelerated bone healing. One study has found that the bone fixation index was only 5-6 days/cm when using motorized and/or automated distraction compared to 22-24 days/cm by manual adjustment.

For example, a motorized strut could be programmed to perform anywhere from one adjustment per day to continuous adjustments. Finer adjustments could increase the number of adjustments over a one-month period from approximately 720 adjustments to approximately 3,600 adjustments (e.g., 6 struts×20 adjustments per day×30 days). Alternatively, finer adjustments could increase the number of adjustments over a one-month period to approximately 259,200 adjustments (e.g., 6 struts×1440 adjustments per day×30 days). Over an extended three-month treatment period, this could increase the number of adjustments from approximately 2,160 adjustments to approximately 10,800 adjustments (e.g., 6 struts×20 adjustments per day×90 days).

Alternatively, finer adjustments could increase the number of adjustments over a three-month period to approximately 777,600 adjustments (e.g., 6 struts×1440 adjustments per day×90 days).

In use, each motorized strut may include a motor and may be used in a spatial frame such as, for example, spatial frame 100, to move the first and second platforms 102, 104, respectively, to align two or more bone portions. In use, the spatial frame and/or system architecture may be arranged and configured to automatically adjust the motorized struts according to the prescribed treatment plan (e.g., automatically adjust the plurality of motorized struts without patient intervention). Alternatively, the spatial frame and/or system architecture may be arranged and configured to require patient and/or caregiver activation to begin the process of automatically adjusting the motorized struts according to the prescribed treatment plan. For example, the spatial frame may be arranged to intermittently auto-adjust the motorized struts at predetermined times according to the treatment plan. Alternatively, the spatial frame may be arranged to intermittently auto-adjust the motorized struts at select times when convenient and/or selected by the patient. Alternatively, the spatial frame may be arranged and configured to continuously auto-adjust the motorized struts in small discrete increments.

Referring to FIG. 2, one known example of a motorized strut 200 is disclosed. In use, for example, the motorized strut 200 may be coupled to first and second platforms in a spatial frame. For example, the motorized strut 200 may be used in place of the manually adjustable struts 106 shown in FIG. 1. As shown in FIG. 2, the motorized strut 200 may include an outer body 202 operatively coupled with a first joint 204 for coupling to a first platform, an inner body 210 operatively coupled with a second joint 212 for coupling to a second platform, and a drive mechanism, actuator, etc. 220 (used interchangeably herein without the intent to limit or distinguish). In use, actuation of the drive mechanism 220 moves the inner body 210 relative to the outer body 202 to adjust a length of the motorized strut 200.

As illustrated, the drive mechanism 220 may include a motor 222 and a threaded rod or lead screw 224 arranged and configured so that, in use, actuation of the motor 222 rotates the threaded rod 224, which moves the inner body 210 relative to the outer body 202 to adjust an overall length of the motorized strut 200. In addition, the drive mechanism 220 may include one or more gears to adjust speed and torque of the motor 222.

In addition, the motorized strut 200 may include any required circuitry. For example, the motorized strut 200 may include one or more position sensors to, for example, monitor absolute position or length of the motorized strut 200. In addition, and/or alternatively, the motorized strut 200 may include other sensors for monitoring various biomechanical parameters such as, for example, a force sensor 230 for monitoring stresses and forces, across the bone gap and/or the soft tissues (muscle, apposing cartilage or peripheral sensory nerves), an accelerometer for capturing patient ambulation data (steps, distance, speed and cadence), a gyroscope for measuring the degree of alignment between the bone fragments, and a sensor motor support 232, etc. In addition, and/or alternatively, the motorized strut 200 may include an encoder such as, for example, a rotary encoder for measuring rotation from the motor 222 for accurate positioning and motion control. In addition, and/or alternatively, the motorized strut 200 may include flash memory for storing unique identifiers (e.g., addresses) and for storing current position, biomechanical and ambulatory data, etc.

As illustrated, the motorized strut 200 may be arranged and configured with an in-line design, wherein the motor 222 shares a common longitudinal axis as the threaded rod 224 and the telescoping portion (e.g., inner body 210) (e.g., the motor and electronics are housed in an enclosure or body that shares the same axis as the threaded rod, adjustment nut, and telescoping portion of the strut).

Additional information on examples of motorized spatial frames can be found in International Patent Application No. PCT/US20/52276, filed on Sep. 23, 2020, published as WO 2021/061816 A1, entitled "Automated Spatial Frame and Automated Struts Used Therewith," the entire contents of said application being hereby incorporated in its entirety herein.

However, automated and/or motorized spatial frames face a number of challenges that need to be overcome. For example, while in-line motorized struts offer a number of design benefits, one problem associated with in-line motorized struts is the relatively lengthy minimum length required of the motorized strut when in the closed or retracted position. That is, in order for the motor to be positioned in-line with the threaded rod, a longer minimum length is needed compared to off-axis or offset designs where the longitudinal axis of the motor is offset from the longitudinal axis of the threaded rod. For example, in use, a treatment plan may require the spacing of the platforms 102, 104 to have a large workable range including a very small minimum distance apart and a very large maximum distance apart. In some instances, an in-line motorized strut may be unable to meet the entire workable range specified by the treatment plan. As a result, the struts may need to be changed out or swapped by other struts during the treatment period to accommodate the full workable range of the spatial frame. Changing out the struts may be tedious and may be uncomfortable to the patient. Designing a motorized strut with an offset axis, wherein the longitudinal axis of the motor is offset or spaced from the longitudinal axis of the threaded rod of the strut enables the motorized strut to have a shorter minimum strut length when in the closed or retracted position.

One example of a spatial frame utilizing a motorized strut is the Robotic Hexapod System manufactured by Orthospin Ltd. The Robotic Hexapod System is a motorized spatial frame that allows real-time physician follow-up and reduce dependence on patient compliance. In use, the Robotic Hexapod System can automatically and continuously adjust and lengthen the struts according to the prescribed treatment plan, without patient involvement. The Robotic Hexapod System utilizes a detachable geared-motor assembly. During use, the detachable geared-motor assemblies can be coupled to custom struts via a first spur gear associated with the motor engaging a second spur gear associated with the threaded rod of the strut. In use, rotation of the motor drives rotation of the threaded rod via the interaction between the first and second spur gears.

The offset motor design of the Robotic Hexapod System enables manual adjustment of the struts during initial construction, setup, assembly, etc. by rotating a knob when the geared-motor assembly is detached from the strut. The Robotic Hexapod System is designed to enable installation of the geared-motor assembly in an out-patient clinic setting. The removable geared-motor assembly are attached in parallel to the threaded rod so that the first and second spur gears can turn the threaded rod in either direction.

However, the offset design of the Robotic Hexapod System from Orthospin, Ltd. suffers from several disadvantages.

First, the detachable geared-motor assemblies are powered and controlled by a wired connection to a centralized controller or control unit, which is coupled on top of the circular hexapod fixation platform. The centralized controller is arranged and configured to control the motor's speed and direction according to the treatment plan. The centralized controller also provides hardware and software protections that prevent any deviation from the treatment plan and alert's the user in case of any malfunctions. Furthermore, the centralized controller also contains the power supply for the entire system and a USB interface to allow a wired connection to a nearby computer. Thus arranged, the motorized spatial frame includes a centralized controller coupled to one of the platforms thereof. The centralized controller including all of the intelligence and power supply for controlling and powering each of the plurality of struts to which the centralized controller is coupled to via a hardwire. In addition, in use, the centralized controller is arranged and configured to communicate with a remote computing device for transmitting and/or receiving data, instructions, etc.

Second, the Robotic Hexapod System does not provide an option for a patient or caregiver to manually adjust the struts. In use, the Robotic Hexapod System is arranged and configured to enable the struts to be manually adjusted only in the operating room by the surgeon. Once the motors are attached, the knob for manual adjustment in the Robotic Hexapod System is physically removed from the device.

A similar motorized spatial frame was disclosed in "Bone mounted hexapod robot for outpatient distraction osteogenesis" by Wendlandt et al. The motorized spatial frame including detachable geared-motor assemblies, which are coupled in parallel to six telescopic struts. In use, the detachable geared-motor assemblies are interchangeable with the manual elements thus allowing easy mounting after the operation. The motor engages the manual strut via gears, which allows the threaded rod to move in either direction to lengthen or shorten the strut. Furthermore, the motorized spatial frame includes a centralized controller or control unit, which is permanently mounted onto one of the platforms to allow for autonomous adjustments of the struts. The centralized controller or control unit is connected to each of the detachable geared-motor assemblies via a digital two-wire bus USB connection providing power and positional data.

Although both designs offer motorized adjustments, the systems are fairly cumbersome and bulky in design for a patient that has to wear the spatial frame for several weeks. In particular, the snagging of the trailing cables, which attaches the detachable geared-motor assemblies to the central controller, provides a safety hazard to the patient.

Thus, it would be beneficial to provide a system that is less bulky and easier to wear. For example, by providing a plurality of geared-motor assemblies that are each arranged and configured as a self-contained unit thereby facilitating distribution of intelligence and power within the system and reduction in weight and bulkiness. In addition, it would be beneficial to provide a system that retains the flexibility of the detachable geared-motor assemblies but eliminates the need for cable connections to provide power, data, and control commands from a centrally located controller. Moreover, by configuring each of the geared-motor assemblies to assume responsibilities for being the primary (e.g., master) assembly to communicate with the external computing device and relay instructions to the remaining secondary (e.g., slave) assemblies, the responsibility of the primary assembly can be transferred during use of the spatial frame to preserve power supply for all assemblies. In addition, by enabling a primary/secondary communication scheme, only one wireless connection needs to be maintained with the external computing device. It is with respect to these and other considerations that the present disclosure may be useful.

SUMMARY OF THE DISCLOSURE

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

A geared-motor assembly arranged and configured to be used in a spatial frame is disclosed. In some examples, the spatial frame includes a plurality of manually adjustable struts coupled to first and second platforms. In use, movement of the struts move the first and second platforms, and hence the first and second bone portions coupled thereto. In any preceding or subsequent example, the struts include an outer body, an inner body, which may be in the form of a threaded rod or lead screw, and an adjustment nut. In use, rotation of the adjustment nut causes the threaded rod to move relative to the outer body to adjust an overall length of the strut.

In accordance with one or more features of the present disclosure, in any preceding or subsequent example, the geared-motor assemblies are arranged and configured to be selectively attached to and detached from the plurality of manually adjustable struts. In use, with the geared-motor assembly detached from the manually adjustable struts, the struts can be manually adjusted (e.g., rotated) to, for example, facilitate initial construction of the spatial frame in the operating room, to allow patients to manually adjust the struts if desired, etc. Thereafter, with the geared-motor assemblies coupled to the struts, motorized and/or automated adjustment of the struts according to a treatment plan can be achieved.

In any preceding or subsequent example, each of the geared-motor assemblies includes a motor having an output shaft and a torque transmitting mechanism arranged and configured to engage the manually adjustable struts. For example, each of the geared-motor assemblies may include a gear such as, for example, a pinon gear, arranged and configured to engage a corresponding gear on the manually adjustable strut so that, in use, activation of the motor rotates the gear on the output shaft of the motor, which rotates the pinion gear coupled to the threaded rod of the strut to facilitate motorized and/or automated adjustment of the struts.

In any preceding or subsequent example, the geared-motor assembly includes a worm-drive mechanism to couple the output shaft of the motor to the threaded rod of the strut. In any preceding or subsequent example, the output shaft of the motor includes, or is formed in, a worm drive. The worm drive being coupled to a first end of an intermediate shaft. A second end of the intermediate shaft including a gear coupled to a corresponding gear on the threaded rod of the strut. In use, activation of the motor rotates the worm drive, which rotates the intermediate shaft, which rotates the threaded rod of the strut.

In any preceding or subsequent example, the gear of the threaded rod and the gear at the second end of the intermediate shaft are beveled gears.

In any preceding or subsequent example, a reduction ratio of between 4:1 to 4096:1 is achieved. In any preceding or subsequent example, a reduction ratio of between 30:1 is achieved.

In any preceding or subsequent example, each of the geared-motor assemblies may include a wireless communication chip arranged and configured to communicate with an external computing system to, for example, exchange data relating to strut position, exchange data relating to and updating the prescribed treatment plan, and exchange data related to the progression of bone healing and frame alignment, etc.

In any preceding or subsequent example, each geared-motor assembly may include a self-contained microprocessor, which can receive and update the treatment plan as needed. In addition, the microprocessor is configured to control operation of the geared-motor assemblies, and hence the struts, without the need for a separate centralized control unit positioned within the spatial frame (e.g., coupled to one of the platforms).

In any preceding or subsequent example, each of the geared-motor assemblies may include a power supply such as, for example, a battery to power the geared-motor assembly including, for example, the motor and any other circuitry contained therein.

In any preceding or subsequent example, the geared-motor assemblies may include a sensor such as, for example, an accelerometer or acoustic emission sensor for detecting faults in the gear train such as, for example, misalignment of the gears (e.g., pinion gears) via vibrational analysis or acoustic emission respectively, which may occur when the geared-motor assembly is removed and re-installed after an X-ray or strut change.

In some examples, a spatial frame is disclosed. The spatial frame including a first platform; a second platform spaced from the first platform; a plurality of adjustable length struts, each of the plurality of adjustable length struts coupled to the first platform and the second platform, each of the adjustable length struts including a housing and a threaded rod, wherein the threaded rod is arranged and configured to move relative to the housing to adjust a length of the strut; and a plurality of geared-motor assemblies, each of the plurality of geared-motor assemblies being arranged and configured to couple to one of the plurality of adjustable length struts, wherein each of the plurality of geared-motor assemblies is arranged and configured as a self-contained unit including electronics and power supply to (i) wirelessly communicate with an external computing device and (ii) to adjust the length of the strut to which it is coupled.

In any preceding or subsequent example, each of the plurality of geared-motor assemblies is devoid of any external wires for coupling to an external controller.

In any preceding or subsequent example, each of the geared-motor assemblies includes a housing; a motor including an output shaft and a gear; a printed-circuit board including a microprocessor and a wireless communication chip; and a power supply arranged and configured to provide power to the motor and printed-circuit board.

In any preceding or subsequent example, one of the plurality of geared-motor assemblies is configured as a primary assembly arranged and configured to communicate with an external computing device to receive instructions and to transmit instructions to the remaining secondary assemblies.

In any preceding or subsequent example, the primary assembly is selectively interchangeable such that responsibilities associated with the primary assembly can be transferred to one of the secondary assemblies.

In any preceding or subsequent example, responsibilities associated with the primary assembly are transferred to one of the secondary assemblies based on remaining power supply of the primary assembly.

In any preceding or subsequent example, responsibilities associated with the primary assembly are transferred to one of the secondary assemblies when a remaining power supply level of the primary assembly is below a threshold value.

In any preceding or subsequent example, responsibilities associated with the primary assembly are transferred to one of the secondary assemblies based on a predetermined schedule.

In any preceding or subsequent example, responsibilities associated with the primary assembly are transferred to one of the secondary assemblies at a predetermined time.

In any preceding or subsequent example, responsibilities associated with the primary assembly are transferred to one of the secondary assemblies based on at least data received by the primary assembly from at least one secondary assembly. The data includes at least one of the following: a power supply level of at least one secondary assembly, a load level of at least one secondary assembly, a frequency of adjustments performed by at least one secondary assembly, a length of adjustments performed by at least one secondary assembly, one or more positioning coordinates of at least one secondary assembly, an angle of adjustments performed by at least one secondary assembly, a direction of adjustments of the at least one secondary assembly, and any combination thereof.

In any preceding or subsequent example, responsibilities associated with the primary assembly are transferred to one of the secondary assemblies based on at least one of: a load data of the primary assembly, a load data of at least one secondary assembly, a power supply level of the primary assembly, a power supply level of the at least one secondary assembly, and any combination thereof.

In any preceding or subsequent example, responsibilities associated with the primary assembly are transferred to one of the secondary assemblies in accordance with a prescription plan determined for the spatial frame.

In any preceding or subsequent example, responsibilities associated with the primary assembly are transferred to one of the secondary assemblies based on an instruction received from one or more external devices communicatively coupled to at least one of the primary assembly and at least one secondary assembly.

In any preceding or subsequent example, each of the plurality of struts include a gear coupled to the threaded rod and each of the plurality of geared-motor assemblies include a housing, a motor including an output shaft and a gear associated therewith, the gear of the motor arranged and configured to be operatively coupled to the gear of the strut.

In any preceding or subsequent example, each of the geared-motor assemblies further include one or more idler gears arranged and configured to engage the gear of the motor and the gear of the strut.

In any preceding or subsequent example, the gear of the strut is at least partially contained within the housing of the strut, the housing of the strut including an opening for providing access to the gear, and the housing of the geared-motor assembly includes an opening to enable one of the gear of the motor and one of the one or more idler gears to extend therethrough.

In any preceding or subsequent example, the housing of the strut further includes a first recess and a peg recess; and the housing of the geared-motor assembly includes a first projection and a spring-loaded peg extending from a surface thereof, the first recess formed in the housing of the strut arranged and configured to receive the first projection of the geared-motor assembly.

In any preceding or subsequent example, wherein, with the first projection received within the first recess, the geared-motor assembly can be rotated relative to the strut.

In any preceding or subsequent example, wherein rotation of the geared-motor assembly relative to the strut causes the spring-loaded peg of the geared-motor assembly to be received within the peg recess.

In any preceding or subsequent example, wherein rotation of the geared-motor assembly relative to the strut causes the spring-loaded peg to contact a ramp formed on the housing of the strut to compress the spring-loaded peg until the spring-loaded peg is aligned with the peg recess.

In any preceding or subsequent example, wherein the housing of the strut further includes a second recess; and the housing of the geared-motor assembly includes a second projection extending from a surface thereof, the second recess formed in the housing of the strut arranged and configured to receive the second projection of the geared-motor assembly.

In any preceding or subsequent example, wherein rotation of the geared-motor assembly relative to the strut causes the second projection to be received within the second recess.

In any preceding or subsequent example, wherein the housing of the strut further includes a removal hole in communication with the peg recess so that a tool can be inserted to facilitate removal of the spring-loaded peg from the peg recess to enable the geared-motor assembly to be disengaged from the strut.

Examples of the present disclosure provide numerous advantages. For example, by providing selectively attachable and detachable geared-motor assemblies, conventional manually adjustable struts can be utilized with only minor design modifications. Because the motors and electronics can be attached after the patient leaves the operating room and they can be removed for imaging, if desired, the risk of adversely affecting the performance of either heat sensitive or chemically sensitive electronics during sterilization or imaging is effectively removed. In addition, the detachable geared-motor assemblies enable the struts to be manually adjusted (e.g., rotated). Thereafter, with the geared-motor assemblies coupled to the struts, motorized and/or automated adjustment of the struts according to a treatment plan can be achieved. Moreover, each of the geared-motor assemblies may be configured as a stand-alone, self-contained device thereby eliminating the need for a separate centralized control unit positioned within the spatial frame (e.g., coupled or positioned on one of the platforms) along with any corresponding wires, cables, etc. to couple the controller to the struts.

Further features and advantages of at least some of the examples of the present disclosure, as well as the structure and operation of various examples of the present disclosure, are described in detail below with reference to the accompanying drawings.

BRIEF DESCRIPTION OF THE DRAWINGS

By way of example, specific examples of the disclosed device will now be described, with reference to the accompanying drawings, in which:

FIGS. 12J-12Q illustrate various views illustrating coupling of a geared-motor assembly to a strut in accordance with one or more features of the present disclosure.

Figure 1:
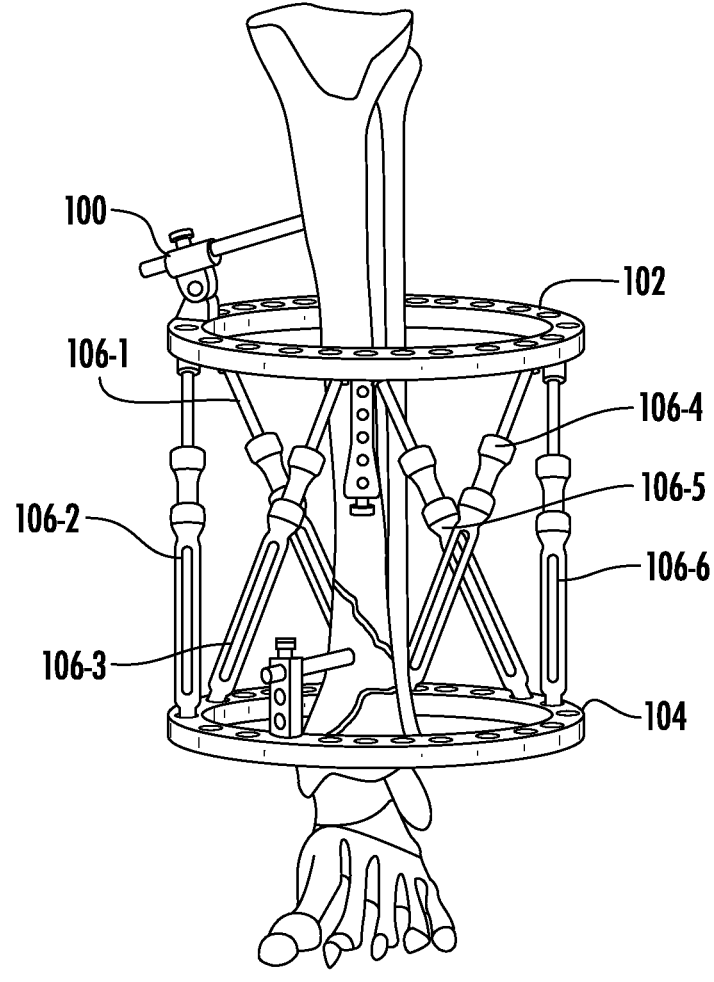
FIG. 1 illustrates a perspective view of a conventional spatial frame including first and second platforms and a plurality of manually adjustable struts coupled thereto.
Figure 2:
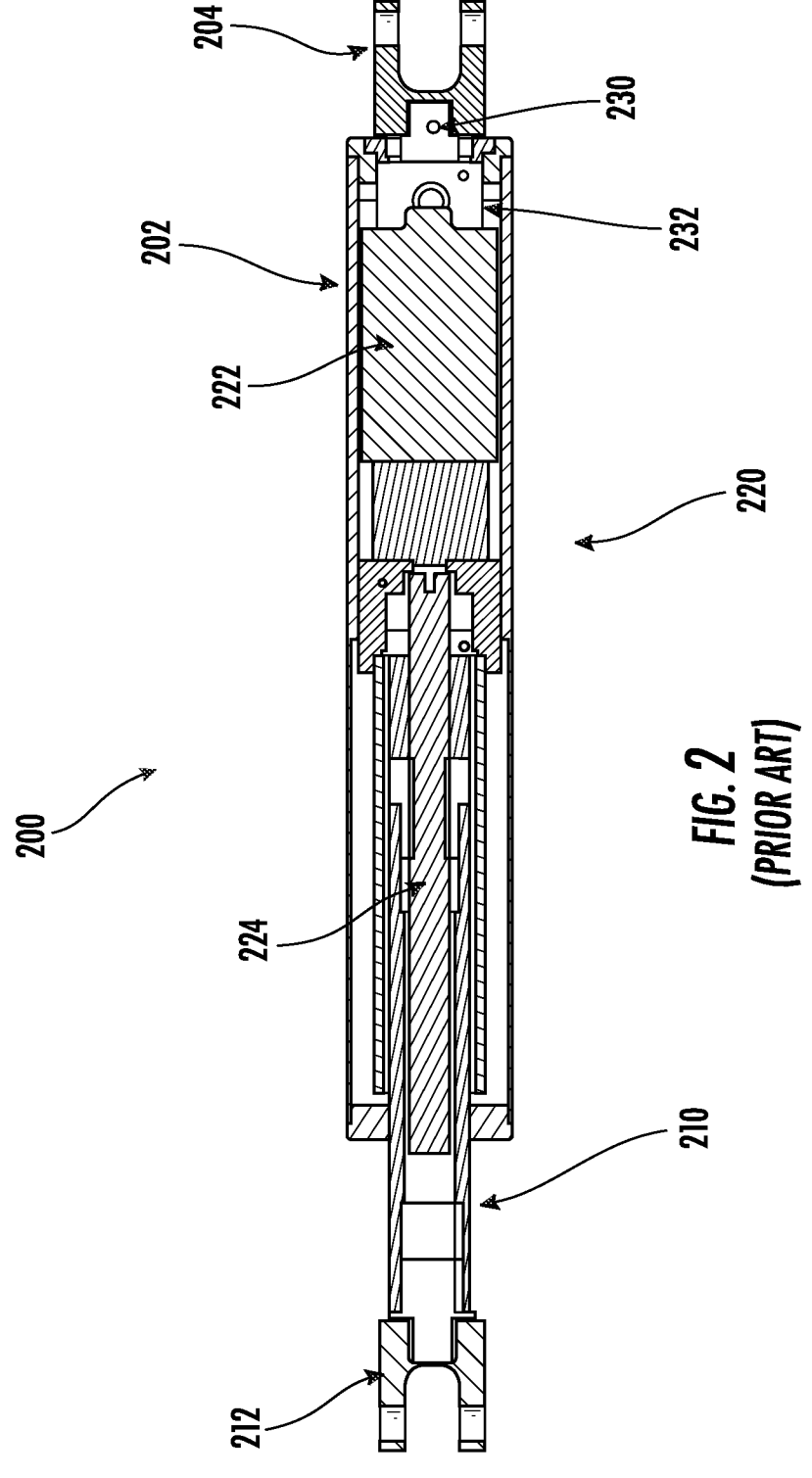
FIG. 2 illustrates a cross-sectional view of a conventional example of a motorized strut that may be used in a spatial frame such as, for example, within the spatial frame shown in FIG. 1.

The drawings are not necessarily to scale. The drawings are merely representations, not intended to portray specific parameters of the disclosure. The drawings are intended to depict various examples of the disclosure, and therefore are not considered as limiting in scope. In the drawings, like numbering represents like elements.

DETAILED DESCRIPTION

Various features or the like of a detachable geared-motor assembly will now be described more fully herein with reference to the accompanying drawings, in which one or more features of the detachable geared-motor assembly will be shown and described. It should be appreciated that the various features may be used independently of, or in combination, with each other. It will be appreciated that the detachable geared-motor assembly as disclosed herein may be embodied in many different forms and may selectively include one or more concepts, features, or functions described herein. As such, the detachable geared-motor assembly should not be construed as being limited to the specific examples set forth herein. Rather, these examples are provided so that this disclosure will convey certain features of the geared-motor assembly to those skilled in the art.

In accordance with one or more features of the present disclosure, a geared-motor assembly is disclosed. As will be described in greater detail herein, in some examples, the geared-motor assembly may be arranged and configured as a self-contained unit arranged and configured to receive and transmit data with an external computing system. The geared-motor assembly including an enclosure or housing containing a motor, a power supply, a microprocessor, and all other power and control circuitry needed to engage and control a manually adjustable strut in a spatial frame.

That is, for example, each geared-motor assembly may include a motor and a torque transmitting mechanism such as, for example, a gear, arranged and configured to engage a corresponding gear on a manually adjustable strut in a spatial frame. In use, actuation of the motor enables motorized rotation of the torque transmitting mechanism and thus the manually adjustable strut coupled to the geared-motor assembly. In addition, each geared-motor assembly may include a microcontroller or microprocessor (terms used interchangeably herein without the intent to limit or distinguish) arranged and configured to control operation of the geared-motor assembly including, for example, receiving and/or updating a treatment plan, and/or controlling activation of the motor without the need for a separate centralized control unit positioned within the spatial frame. Each geared-motor assembly may further include a wireless communication chip or antenna arranged and configured to communicate with an external computing system to, for example, exchange data relating to strut position, exchange data relating to and updating the prescribed treatment plan, etc. Each geared-motor assembly may also include a power supply such as, for example, batteries, to power the geared-motor assembly including, for example, the motor, the microcontroller, the wireless communication chip, and any associated sensors and/or additional circuitry. Each geared-motor assembly may also include a sensor for either positional control, biomechanical feedback, or a fault level detection in the gear train. Thus arranged, in some examples, each geared-motor assembly may include its own self-contained power management, wireless communication, and microcontroller unit that controls the position of the strut.

As will be described in greater detail, in use, the detachable geared-motor assemblies are arranged and configured to be used in a spatial frame. In use, the spatial frame includes a plurality of manually adjustable struts coupled to first and second platforms. In use, movement of the struts move the first and second platforms, and hence the first and second bone portions coupled thereto. For example, with reference to FIG. 3A, an example of a spatial frame 300 is illustrated. As previously mentioned, the spatial frame 300 includes a first platform such as, for example, first platform 102, a second platform such as, for example, second platform 104, and a plurality of manually adjustable struts such as, for example, struts 106, coupled to the first and second platforms 102, 104.

In use, each of the detachable geared-motor assemblies may be coupled to one of the manually adjustable struts. Thus arranged, the spatial frame can be selectively configured to operate in either of a first or manually adjustable mode or configuration of operation wherein each strut may be manually adjusted or a second or motorized mode or configuration of operation wherein a geared-motor assembly may be coupled to each strut to facilitate motorized adjustment of the struts. Thus arranged, in use, the plurality of struts can be manually adjusted. In addition, by coupling a geared-motor assembly to strut, the adjustments can be motorized and/or automated, thereby providing greater flexibility to doctors and patients in carrying out the prescribed treatment plan.

In addition, in use, by utilizing a detachable geared-motor assembly that couples to a manually adjustable strut by, for example, interconnecting corresponding gears, an offset motor design is achieved thereby enabling a shorter minimum strut length to be achieved (e.g., the geared-motor assemblies and struts may be arranged and configured with a shorter minimum length (e.g., length of the strut as measured end to end (e.g., joint to joint) with the threaded rod assembly in the fully retracted position) as compared to conventional in-line motorized struts, while still providing a reasonable working length (e.g., adjustment length of the strut in use-length adjustment or difference between the minimum length and the maximum length of the strut).

Figure 3A:
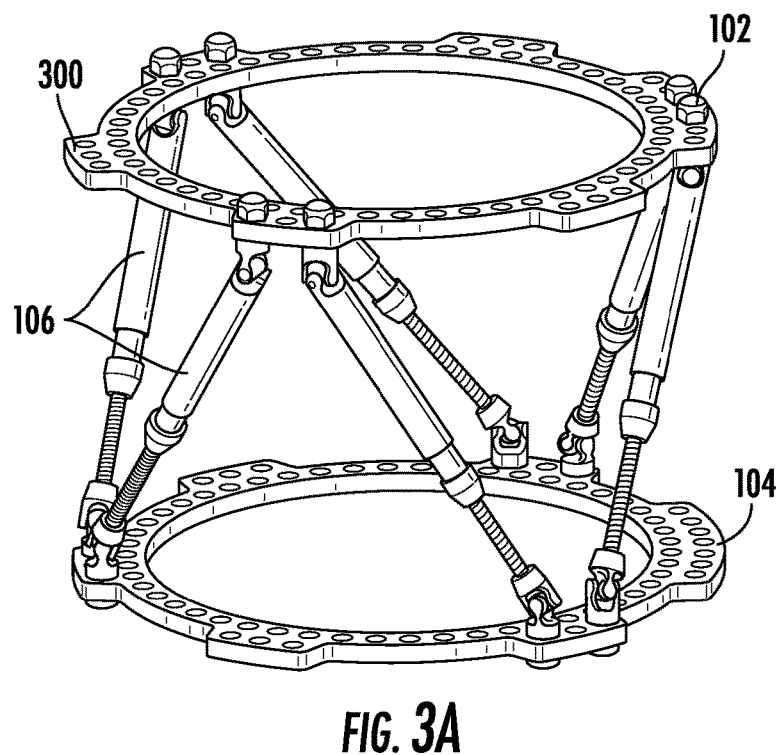
FIG. 3A illustrates a perspective view of an alternate conventional spatial frame including first and second platforms and a plurality of manually adjustable struts coupled thereto.
Figure 3B:
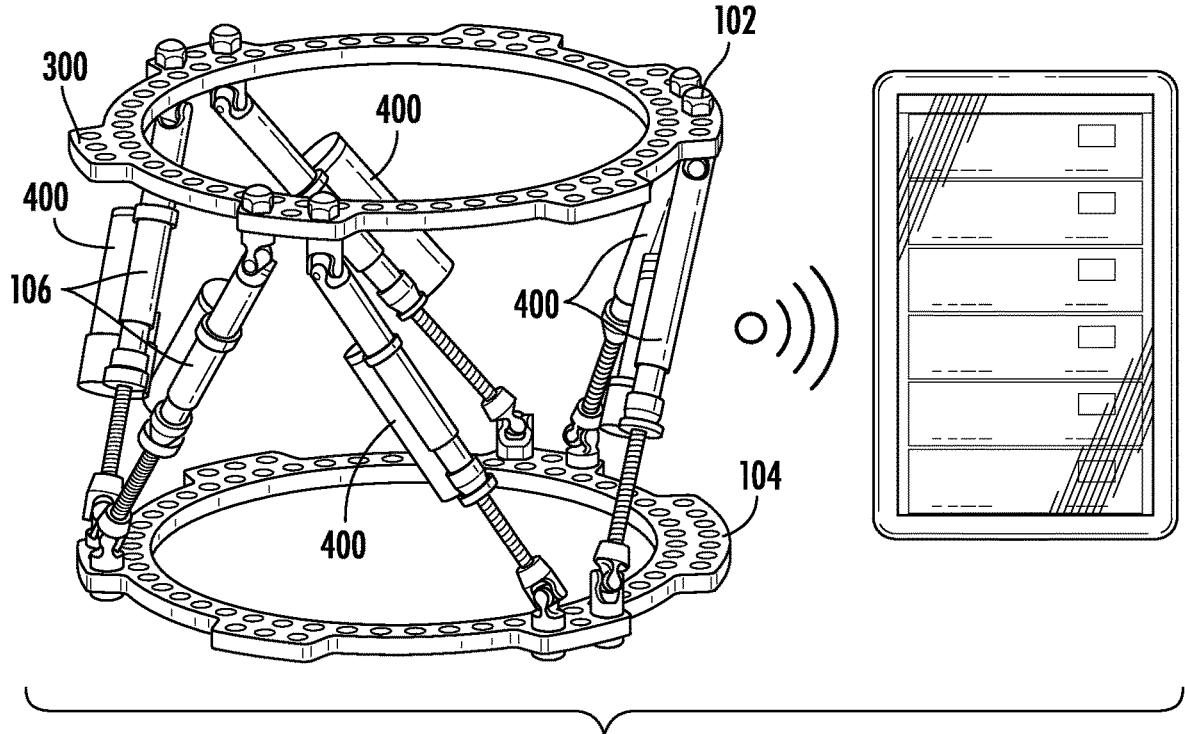
FIG. 3B illustrates a perspective view of an example of a spatial frame including a plurality of geared-motor assemblies coupled to the manually adjustable struts of the spatial frame in FIG. 3A in accordance with one or more features of the present disclosure, the spatial frame including the plurality of geared-motor assemblies and a companion APP to transmit and receive data, instructions, and updates.

With additional reference to FIG. 3B, in use, the removable geared-motor assembly 400 is arranged and configured to engage, attach, couple, etc. to the manually adjustable struts 106 of the spatial frame 300. Thus arranged, the spatial frame 300 can be operated in and switched between two modes or configurations of operation. In the first mode or configuration of operation, the struts 106 may be manually adjustable as illustrated in FIG. 3A. In the second mode or configuration of operation, a geared-motor assembly 400 may be attached to one or more of the manually adjustable struts 106 to enable motorized and/or automated adjustment of the struts.

In use, the geared-motor assemblies 400 are coupled to the manually adjustable struts 106 of the spatial frame 300. In some examples, the geared-motor assemblies 400 may be coupled to the manually adjustable struts 106 after surgery in clinic by, for example, a primary care provider. Alternatively, the geared-motor assemblies 400 may be coupled to the manually adjustable struts 106 at any time and by anyone. Once coupled, the geared-motor assemblies 400 may facilitate motorized and/or automated adjustments such as, for example, semi-continuous actuation. For example, the geared-motor assemblies 400 may enable motorized adjustments to be made autonomously via a companion APP running on, for example, a smartphone, a tablet, or other external computing system. Thus arranged, the spatial frame and/or system architecture may be arranged and configured to automatically adjust the motorized struts according to the prescribed treatment plan (e.g., automatically adjust the plurality of struts without patient intervention). Alternatively, and/or in addition, the spatial frame and/or system architecture may be arranged and configured to require patient and/or caregiver activation to begin the process of automatically adjusting the struts according to the prescribed treatment plan. For example, the spatial frame may be arranged to intermittently auto-adjust the motorized struts at predetermined times according to the treatment plan. Alternatively, the spatial frame may be arranged to intermittently auto-adjust the motorized struts at selected times when convenient and/or when selected by the patient.

As will be described in greater detail herein, in accordance with one or more features of the present disclosure, the geared-motor assemblies 400 may each include an enclosure or housing 410, a coupling mechanism 420 for coupling the geared-motor assembly 400 to the strut 106, a motor 430, a torque transferring mechanism 431 (e.g., a transmission or gears for transferring rotation from the motor 430 to the strut 106), and all necessary components and circuitry so that activation of the motor 430 moves the strut 106. For example, the gear-motor assemblies 400 may include one or more microprocessors, sensors such as, for example, positional sensors to monitor the length of the struts, load sensors or accelerometer for providing biomechanical feedback during bone healing and acoustic emission or vibration sensor for fault level detection in the gear train, a wireless communication chip or antenna for facilitating wireless communication and/or transfer of data, a power supply such as, for example, a battery, a charging circuit, etc.

Thus arranged, in accordance with one or more features of the present disclosure, a number of advantages are achieved. For example, by utilizing detachable geared-motor assemblies 400, motorized and/or automated adjustments of a spatial frame can be achieved. In use, the detachable geared-motor assemblies 400 are arranged and configured to engage a manually adjustable strut 106 in an outpatient setting thus enabling the spatial frame to be operated in two different modes or configurations: (a) a standard, manual adjustment mode where the lengths of the struts 106 can be adjusted by manual rotation of a threaded adjustment nut and (b) motorized and/or automated adjustment via the detachable geared-motor assemblies 400.

In addition, in accordance with one or more features of the present disclosure, by arranging the geared-motor assemblies 400 as self-contained units or devices incorporating wireless, self-powered, and incorporating their own microprocessors (e.g., in some examples, the geared-motor assemblies 400 are arranged and configured as a self-contained unit including all of the necessary components and circuitry to control each strut according to the prescribed treatment plan), the geared-motor assemblies eliminate the need for any external cables or wires that could snag during use and eliminate the need for incorporating a centralized control unit onto one of the platforms of the spatial frame thereby reducing bulk and safety risk to the patient (e.g., self-containment of the control circuitry, wireless communication chip, and power source within geared-motor assemblies negate the need for cables and a centralized control unit positioned elsewhere on the spatial frame along with any needed cables or wires).

In addition, by utilizing detachable geared-motor assemblies, existing features of the manually adjustable struts are retained. That is, with the geared-motor assemblies detached from the manually adjustable struts, operation of the struts is unaffected. For example, if the manually adjustable strut incorporates a quick adjustment feature (e.g., quick adjustment nut 122 in FIG. 5B) to enable manual lengthening of the strut without rotating the threaded nut or rod, such adjustment feature is retained thus enabling faster adjustment during, for example, initial setup in the operating room. Moreover, the detachable geared-motor assemblies provide an offset motor design allowing greater application or use. For example, by incorporating an offset motor design, a shorter minimum strut length can be achieved (approximately 80 mm), which allows the struts to be used for correcting deformities in, for example, children with shorter limbs.

As previously mentioned, in some examples, when arranged in a spatial frame, the geared-motor assemblies may be arranged and configured to wirelessly exchange data, instructions, etc. with an external computing system such as, for example, a smartphone, a tablet, a computer, etc. running a companion APP. However, it is envisioned that the geared-motor assemblies may exchange data with an external computing system by any now known or hereafter developed system. For example, each of the geared-motor assemblies may include a communication interface to exchange data over a wired connection. Thus arranged, in some examples, one or more of the geared-motor assemblies can receive, download, etc. the prescription via a hardwire connection, although this is but one configuration and others are envisioned.

In some examples, the geared-motor assemblies may be water-proofed to facilitate the patient, for example, taking a shower or bath. Alternatively, it is envisioned that the detachable geared-motor assemblies could be removed prior to showering and/or the spatial frame may be covered by, for example, a bag during a shower thus alleviating the necessity for waterproofing each of the geared-motor assemblies. The detachable geared-motor assembly may also eliminate the need for sterilization since the geared-motor assemblies can be coupled to the struts in clinic.

Figure 4:
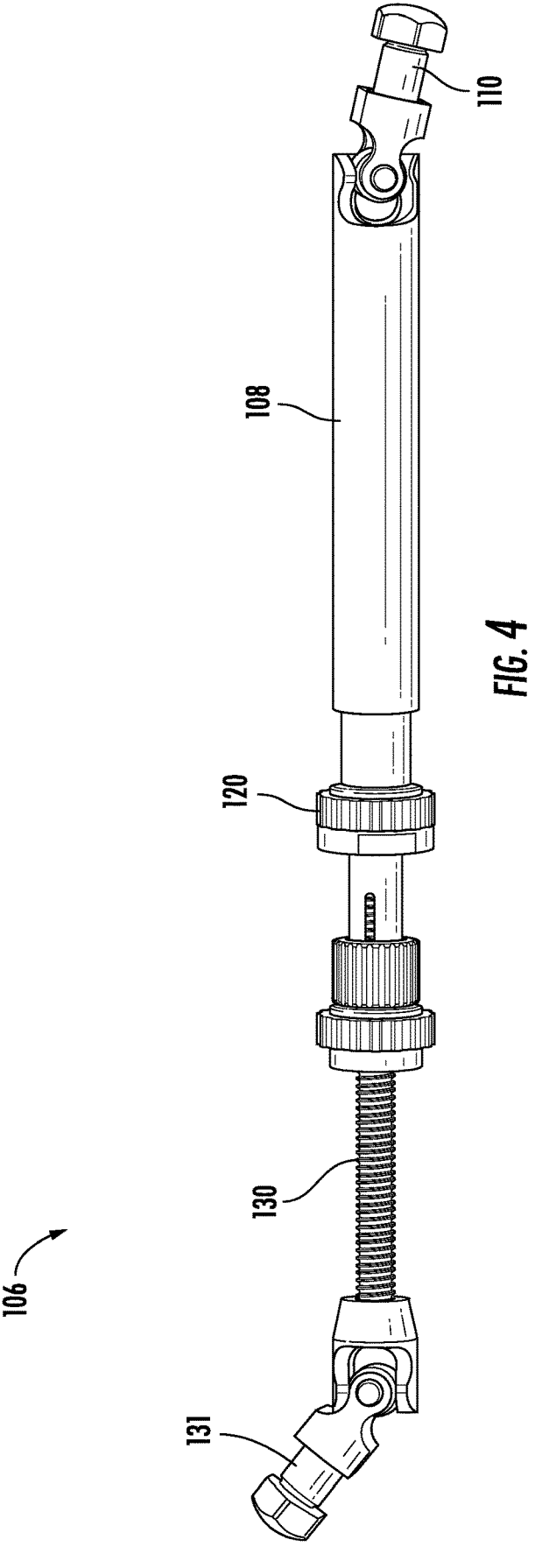
FIG. 4 illustrates a side view of a conventional manually adjustable strut.

With reference to FIG. 4, an example of a conventional manually adjustable strut such as, for example, strut 106, is shown. As will be readily appreciated by one of ordinary skill in the art, the manually adjustable strut 106 includes an outer body 108 including a first joint 110 for coupling to a first platform, an internally threaded member or adjustment nut 120 coupled to the outer body 108, and an externally threaded rod or lead screw 130 including a second joint 131 for coupling to a second platform, the externally threaded rod 130 threadably engaging the adjustment nut 120. In use, the externally threaded rod 130 is constrained such that it cannot rotate relative to the outer body 108, the adjustment nut 120 is rotatably coupled to the outer body 108 but cannot translate. Thus arranged, in use, rotation of the adjustment nut 120 causes the externally threaded rod 130 to move (e.g., translate) relative to the outer body 108 to lengthen or shorten the length of the strut 106 depending on the direction of rotation. As previously mentioned, during use, the adjustment nut 120 can be manually rotated, for example, by hand or using a wrench.

In accordance with one or more features of the present disclosure, by coupling a motor to the strut 106, motorized and/or automated adjustment of the strut 106 can be achieved. For example, with reference to FIGS. 5A and 5B, the adjustment nut 120 could be modified to include teeth into an outer diameter thereof. Alternatively, the adjustment nut 120 could be replaced with a gear or the strut 106 could be modified to include a gear coupled to the threaded rod 130. In any event, in use, an interface is created for coupling the motor 430 of the detachable geared-motor assembly 400 to the strut 106.

Figure 5A:
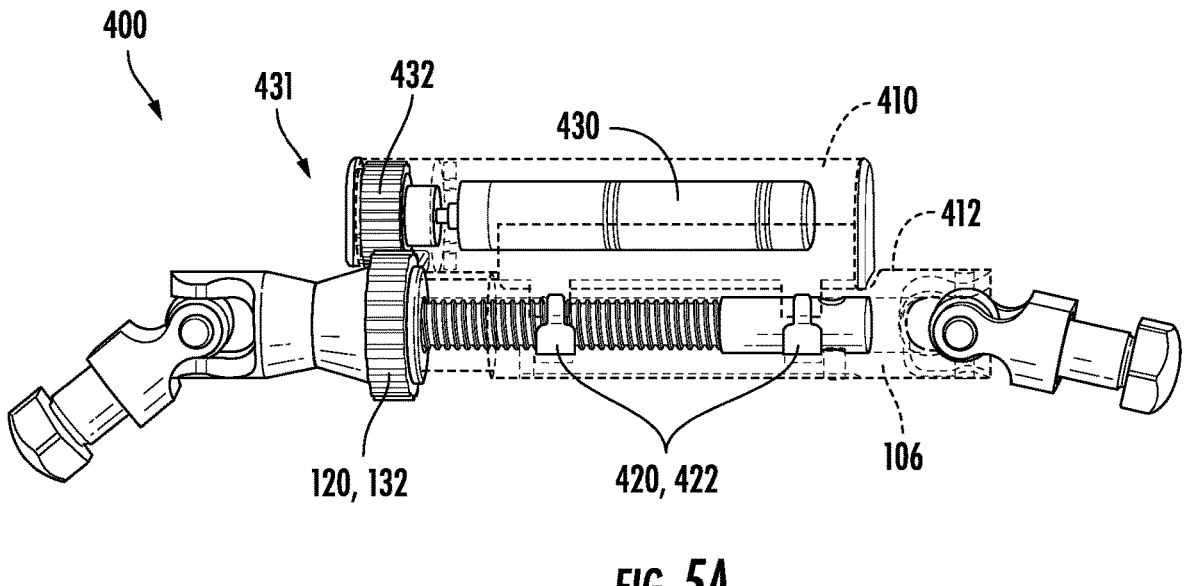
FIGS. 5A and 5B illustrate various views of an example of a geared-motor assembly in accordance with one or more features of the present disclosure, the geared motor assembly being coupled to a manually adjustable strut.
Figure 5B:
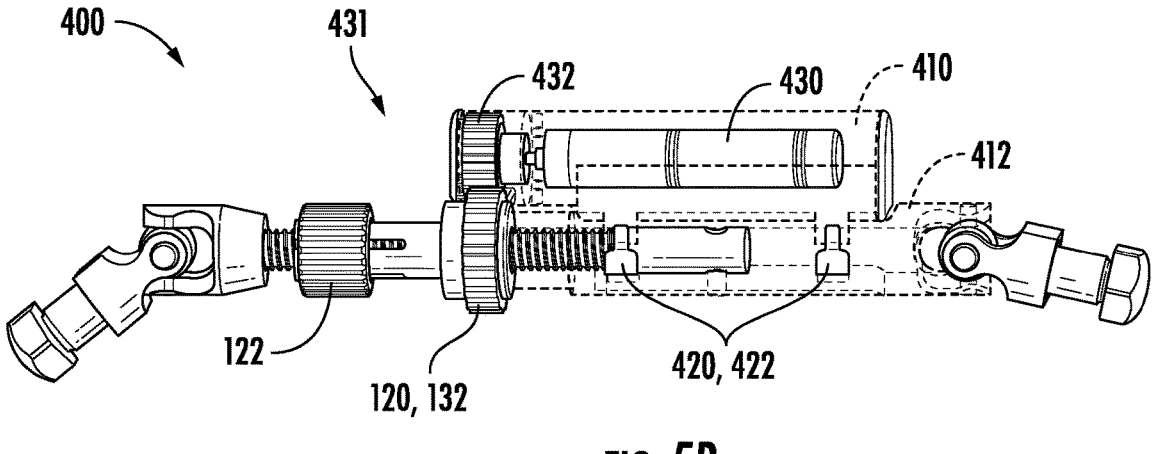

With reference to FIGS. 5A and 5B, in accordance with one or more features of the present disclosure, examples of a geared-motor assembly 400 will be shown and described. As shown, the geared-motor assemblies 400 include a housing or enclosure 410 (terms used interchangeably herein within the intent to limit or distinguish). In use, the housing 410 is arranged and configured to enclose, or at least partially enclose, all of the components of the geared-motor assembly 400. For example, with additional reference to FIG. 9, the geared-motor assembly 400 includes a control circuit 450 (e.g., a printed-circuit board (PCB)), a micro-controller 452, a wireless communication chip, a power supply 454 such as, for example, one or more batteries, and an optional charging circuit 456). The electronics and the power source being housed with the motor 430 inside the housing 410. In use, when properly coupled to each of the struts 106, the geared-motor assemblies 400 facilitate motorized and/or automated adjustment of the strut 106. In addition, the geared-motor assemblies 400 may be coupled (e.g., wirelessly coupled) to an external computing system running, for example, a companion APP.

In some examples, the geared-motor assemblies 400 may include an IP-68 rated housing manufactured from any suitable material including, for example, a metal or metal alloy, a polymer, a light-weight material such as PEEK, nylon, aluminum, etc. In addition, the housing may be manufactured via any now known or hereafter developed technique such as, for example, injection molding, additive manufacturing, etc.

In use, the geared-motor assembly 400 can be mounted to the manual struts 106 via a coupling mechanism 420, which can be arranged in any suitable mechanism now known or hereafter developed to couple or mount the geared-motor assemblies 400 to the struts 106 including, for example, clips, sleeves, magnets, straps, feet and spring-loaded pegs (as will be described in greater detail below), etc. In some examples, the coupling mechanism 420 enables attachment and detachment of the geared-motor assembly 400 from the strut 106 to facilitate a change in mode between manual and automated adjustment. In some examples, with continued reference to FIGS. 5A and 5B, the geared-motor assembly 400 may include spring loaded arms 422 arranged and configured to enable the geared-motor assembly to clip onto or engage the outer body 108 of the strut 106. As illustrated, in some examples, in order to better accommodate the geared-motor assembly 400, the outer body 108 of the strut 106 may be modified to include a flat surface and/or grooves

412 formed in the outer surface thereof. Thus arranged, by modifying a conventional strut to include a gear or gear teeth and optionally modifying the strut to include one or more flats and/or grooves for accommodating the geared-motor assembly 400, the modified conventional strut could be used for both manual and motorized adjustment cases.

Figure 6A:
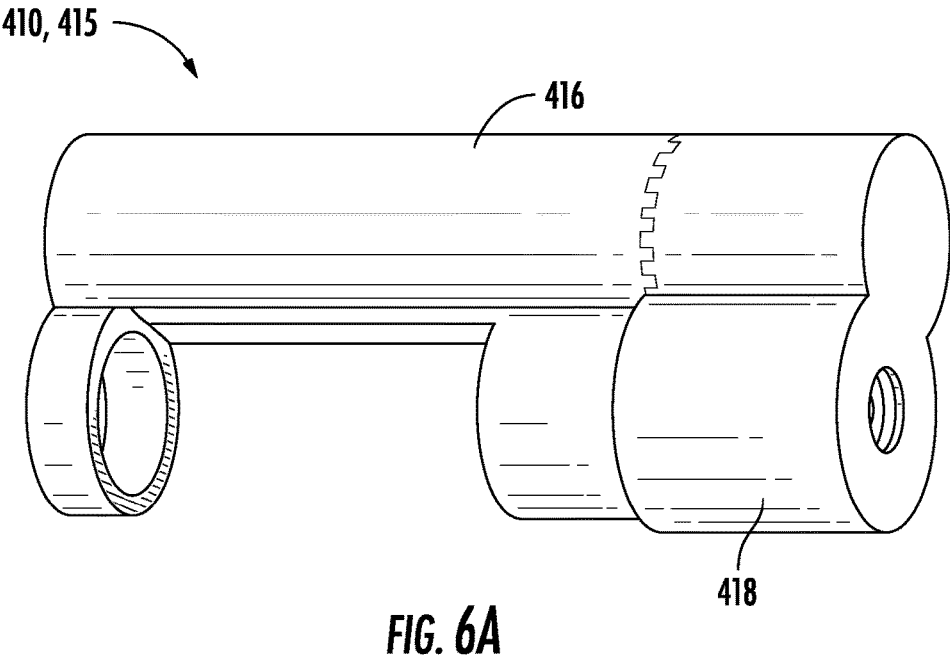
FIG. 6A illustrates a perspective view of an example of a housing of a geared-motor assembly in accordance with one or more features of the present disclosure.
Figure 6B:
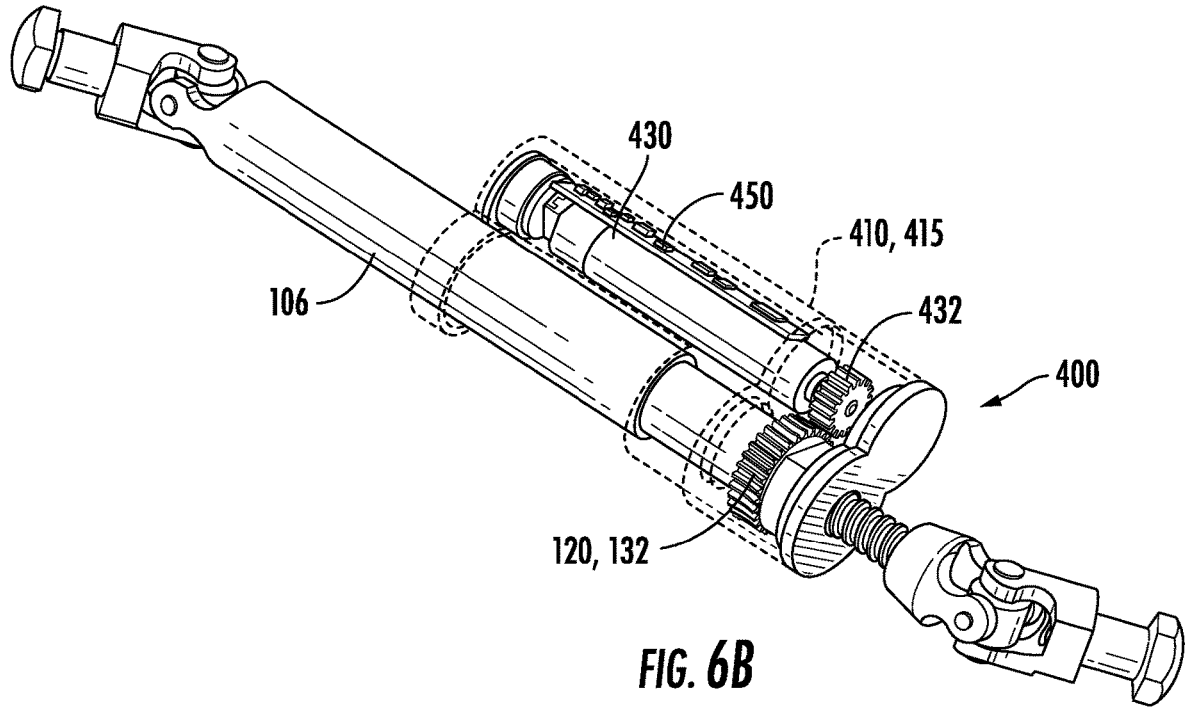
FIG. 6B illustrates a perspective view of a geared-motor assembly using the housing of FIG. 6A coupled to a manually adjustable strut in accordance with one or more features of the present disclosure.
Figure 6C:
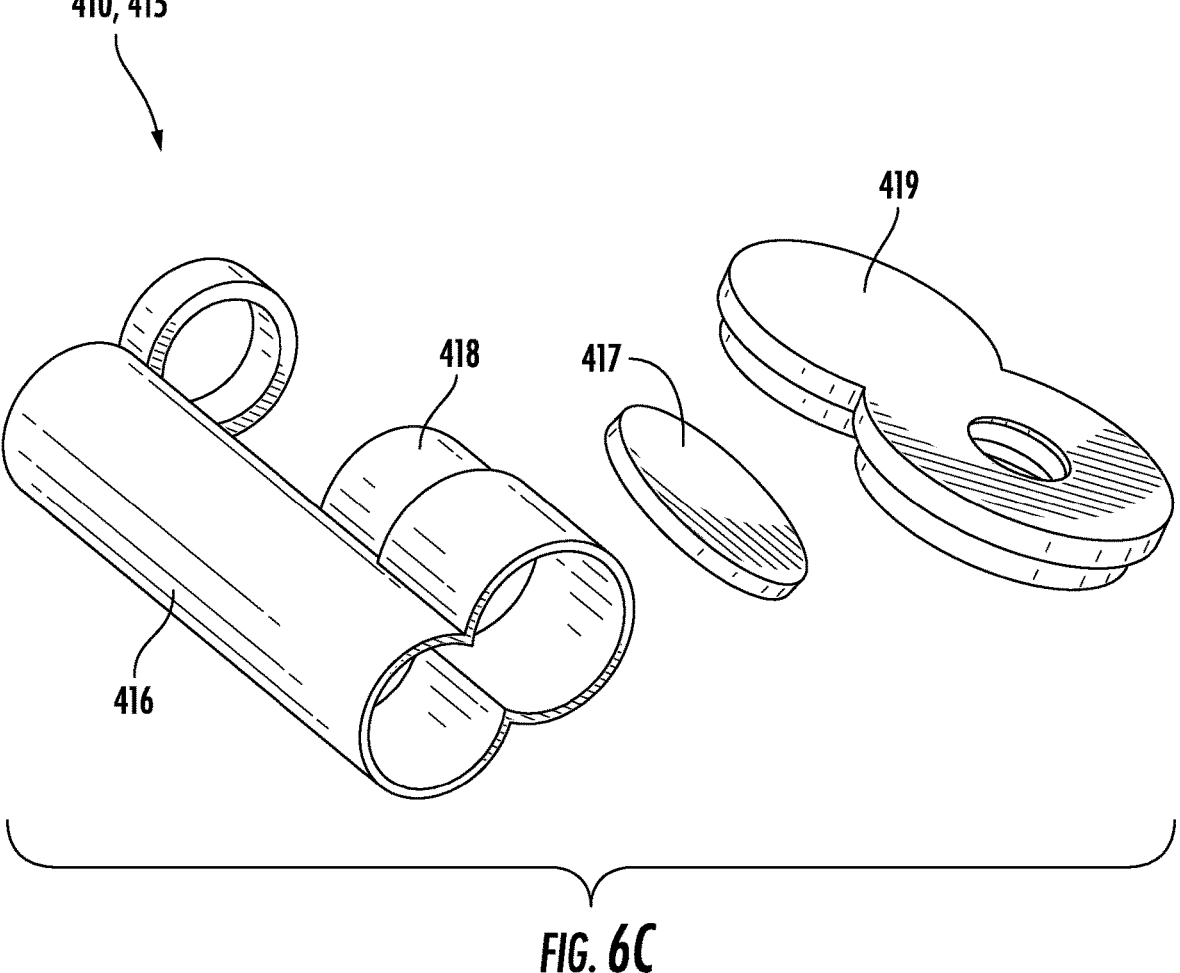
FIG. 6C illustrate an exploded perspective view of the housing shown in FIG. 6A.

Alternatively, with reference to FIGS. 6A-6C, in some examples, the housing 410 of the detachable geared-motor assembly 400 may be provided in the form of an outer casing or sleeve 415. As illustrated, in some examples, the outer casing or sleeve 415 includes a first housing portion 416 arranged and configured to receive the motor 430 and a second housing portion 418 arranged and configured to receive the strut 106. In use, the outer casing or sleeve 415 is arranged and configured to accommodate the motor 430 and the manual strut 106 in parallel. The outer casing or sleeve 415 may further include a battery lid 417 and a motor lid 419. In use, with the motor 430 positioned within the first housing portion 416 of the outer casing or sleeve 415 and with the strut 106 positioned within the second housing portion 418, the threaded rod 130 of the strut 106 may extend through a threaded hole formed in the motor lid 419. A gasket or O-ring can be used to help seal the threaded hole thereby preventing any moisture ingress into the geared-motor assembly 400. Once properly positioned the gear 432 of the motor 430 may be positioned into engagement with the gear or adjustment nut 120 of the strut 106 so that activation of the motor 430 rotates the threaded rod 130 of the strut 106.

In an alternate example, it is envisioned, that the geared-motor assembly 400 may be permanently coupled to the strut 106 thereby eliminating the need for the coupling mechanism. A fully consolidated design with an offset motor would still provide the benefit of shorter minimum strut length. However, such design, would likely require sterilization of the entire device including the motor, gears, battery and electronics.

In any event, regardless of the housing or coupling mechanism being utilized, the geared-motor assembly 400 includes a motor 430 such as, for example, a DC brushless or brushed geared motor or a stepper motor, a torque transmitting mechanism 431 such as, for example, a gear 432 operatively coupled to an output shaft 434 of the motor 430, and all necessary components and circuitry so that activation of the motor 430 moves the threaded rod 130 of the strut 106.

In use, the motor 430 can be any suitable motor now known or hereafter developed. For example, with reference to Table 1, reprinted below, various example of miniature motors that can be used are provided as examples to illustrate ranges in axial thrust performance.

Figure 7:
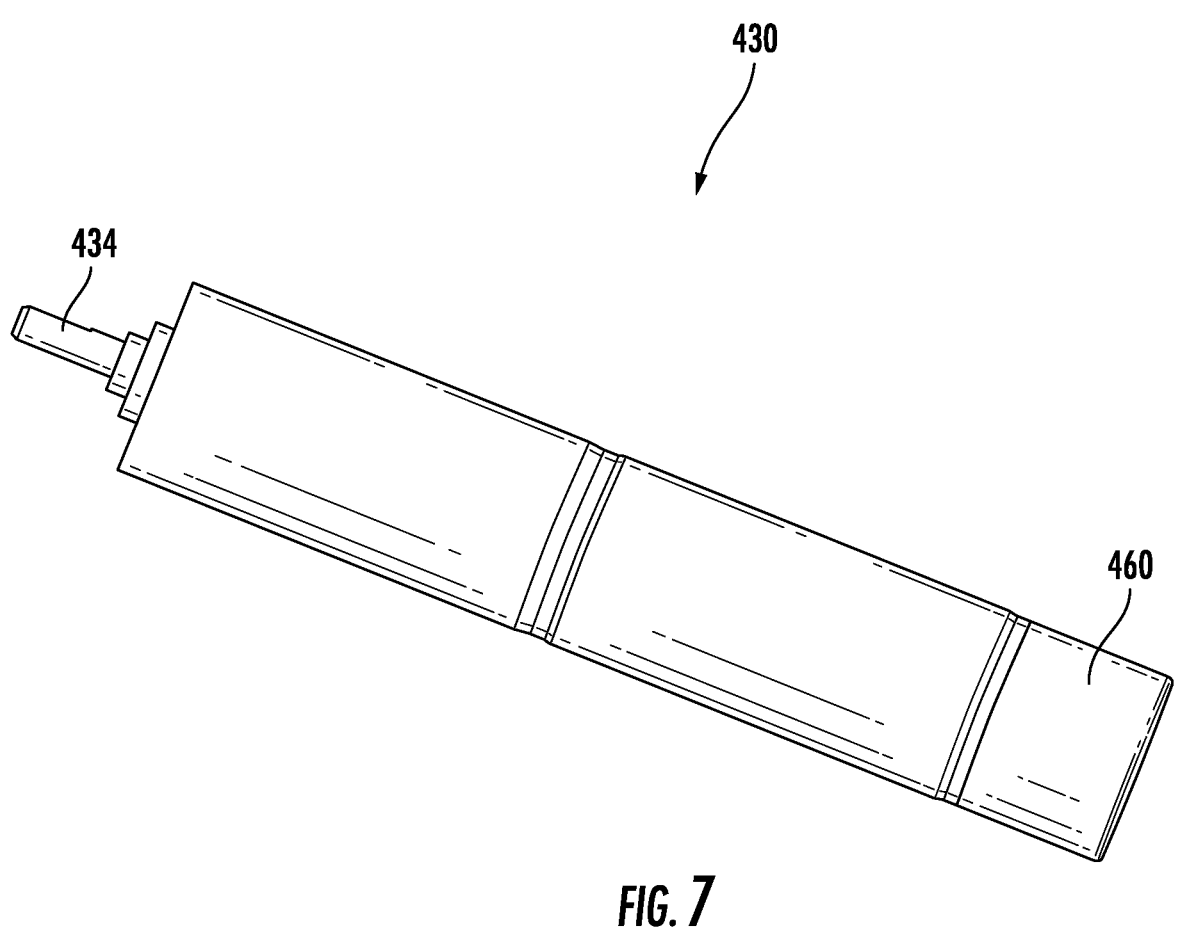
FIG. 7 illustrates a perspective view of an example of a motor that may be used in a geared-motor assembly in accordance with one or more features of the present disclosure.

In some examples, the motor 430 may be a high power density DC motor having, for example, a diameter between 4 and 12 mm. In one particular example, as illustrated in FIG. 7, the motor 430 may be a 8 mm×39 mm DC brushless motor manufactured by Maxon having a nominal voltage and gear reduction of 12V and 1296:1 respectively. In an alternative example, the motor 430 could be a 10 mm×37 mm geared stepper motor manufactured by Portescap, which is configured to operate at low speeds with high precision and higher holding torque. Thus arranged, the motor 430 may be arranged and configured to produce an output torque of 3826 mNm and a theoretical axial thrust between 4450 and 6800N (i.e., for the 8 mm diameter brushless motor manufactured by Maxon (B7D0B83148C1) (see table 1 below) depending on the pitch of the threaded rod 130 and the surface finish of the mating parts. As illustrated, and as will be described in greater detail herein, the motor 430 may include one or more sensors 460 such as, for example, an optical encoder or Hall effect sensor for tracking strut position, a vibrational sensor or acoustic emission sensor for fault detection in the gear train and a load sensor or accelerometer for tracking bone healing and frame alignment relative to the bone fragments.

TABLE 1

Theoretical torque values for the 4-, 6-, and 8- mm diameter Maxon and 15 mm diameter Faulhaber motors determined from motor datasheets.
COF = Coefficient of Friction. The efficiency of the BLDC motors is less in pulse mode compared to continuous mode due to stick-slip friction.
The capability of the motor to drive against the load is defined by the output torque the motor can create multiplied by the gear ratio

| Motor Configuration | Theoretical Gearbox Data | | | | Theoretical Motor Data | | | |
| | Gearhead Ratio (GR) | Gearhead Max Efficiency % (E) | Max Continuous Torque (mN · m) | Max Intermittent Torque (mN · m) | Stall Current (A) | Stall Torque (ST) (mNm) | Output Torque (GR × ST × E) (mNm) | Theoretical Axial Thrust (N) |
|---|---|---|---|---|---|---|---|---|
| Faulhaber motor 1515U012B IE2-8 | 324:1 | 53 | 30 | 50 | n/a | 0.904 | 155.2 | |
| 4 mm dia. brushless motor - Medium size (B7DQB8310323) | 280:1 | 65 | 15 | 20 | 0.264 | 0.403 | 73.4 | Stall torque for motor-gearbox combination of 0.403 × 280 = 112.8 mNm 65% efficiency: 0.65 × 112.8 = 73.3 mNm. 4 mm leadscrew with COF = 0.25 (dry steel on bronze) and a pitch of 0.7 mm; thrust of 200N with a torque of 116 mNm |
| 6 mm dia. brushless Maxon motor (B7D0B831226A) | 854:1 | 52 | 30 | 60 | 0.97 | 1.7 | 754.9 | 6 mm leadscrew (1 mm pitch): Unlubricated (COF = 0:23): 880N Lubricated (COF = 0.16): 1170N 6 mm leadscrew (0.5 mm pitch): Unlubricated (COF = 0.23): |

TABLE 1-continued

Theoretical torque values for the 4-, 6-, and 8- mm diameter Maxon and 15 mm diameter Faulhaber motors determined from motor datasheets.
COF = Coefficient of Friction. The efficiency of the BLDC motors is less in pulse mode compared to continuous mode due to stick-slip friction.
The capability of the motor to drive against the load is defined by the output torque the motor can create multiplied by the gear ratio

| Motor Configuration | Theoretical Gearbox Data | | | | Theoretical Motor Data | | | |
| | Gearhead Ratio (GR) | Gearhead Max Efficiency % (E) | Max Continuous Torque (mN · m) | Max Intermittent Torque (mN · m) | Stall Current (A) | Stall Torque (ST) (mNm) | Output Torque (GR × ST × E) (mNm) | Theoretical Axial Thrust (N) |
| --- | --- | --- | --- | --- | --- | --- | --- | --- |
| 8 mm dia. brushless Maxon motor (B7D0B83148C1) | 1296:1 | 57 | 40 | 60 | 1.43 | 5.18 | 3826 | 975N Lubricated (COF = 0.16): 1340N 6 mm leadscrew (1 mm pitch): Unlubricated (COF = 0.23): 4450N Lubricated (COF = 0.16): 5900N 6 mm leadscrew (0.5 mm pitch) Unlubricated (COF = 0.23): 4950N Lubricated (COF = 0.16): 6800N |

As previously mentioned, in some examples, the geared-motor assembly 400 includes a torque transferring mechanism 431 for transferring torque from the motor 430 to the strut 106. In use, the torque transferring mechanism 431 can be any suitable mechanism now known or hereafter developed. For example, as previously described, the strut 106 and the motor 430 may include first and second gears 132, 432, respectively. In use, the first gear 132 is operatively associated with the strut 106. The second gear 432 is operatively associated with the motor 430 so that activation of the motor 430 drives (e.g., rotates) the second gear 432, which rotates the first gear 132 thereby translating the threaded rod 130 of the strut 106.

In use, the first and second gears 132, 432 may be any suitable gear now known or hereafter developed. For example, the first and second gears 132, 432 may be pinon gears, spur gears, helical gears, a worm gear mechanism (as will be described in greater detail below), etc. Alternatively, the torque transferring mechanism 431 may be a belt drive system. With general reference to FIGS. 5A, 5B, 6B, and 8, in some examples, the adjustment nut 120 of the strut 106 can be modified to include an external-toothed geared surface thereby transitioning the adjustment nut 120 of the strut 106 into the first gear 132 so that the adjustment nut 120 of the strut 106 can be directly driven by the gear 432 attached to the output shaft 434 of the motor 430. Alternatively, the strut 106 can include a gear (e.g., the first gear 132). For example, the first gear 132 can be mounted on the threaded rod 130. In some examples, the first gear 132 can be mounted on the threaded rod 130 as a compression-fitted collar. In use, the first gear 132 engages with the second gear 432 located on the output shaft 434 of the motor 430. Thus arranged, activation of the motor 430 rotates the second gear 432, which rotates the first gear 132, which causes the strut 106 to move.

In some examples, and as previously mentioned, the geared-motor assembly 400 may include a control circuit 450. The control circuit 450 may be arranged and configured to enable autonomous, ultra-low speed movement of the strut (0.002 mm/s) and a survey of the mechanical loads exerted on the motor 430 through computation of the motor torque (DC motor current correlates with torque load on motor).

Figure 8:
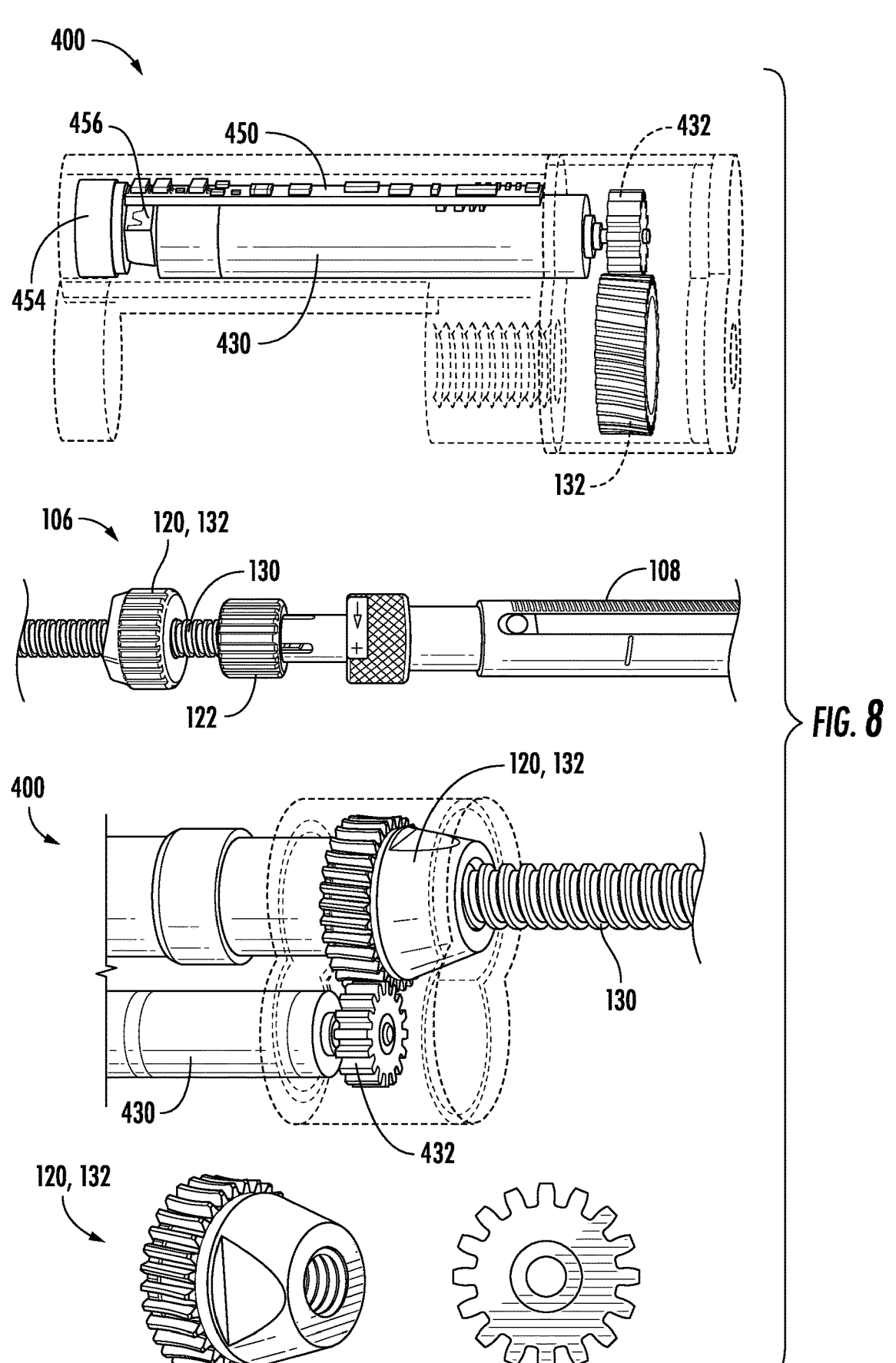
FIG. 8 illustrates various views of an example of a geared-motor assembly in accordance with one or more features of the present disclosure, the FIGURES illustrating the coupling of the geared-motor assembly to the strut including the engagement of the corresponding gears.
Figure 9:
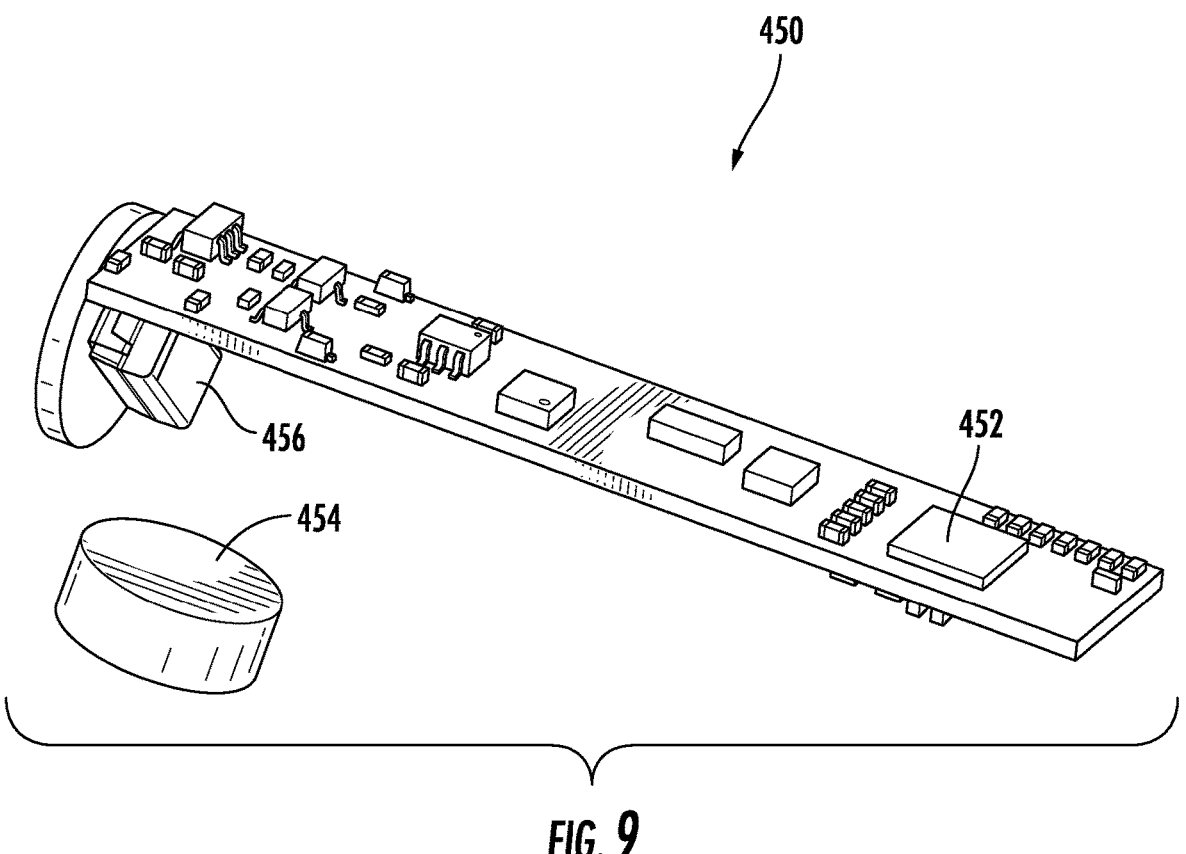
FIG. 9 illustrates a perspective view of an example of a control circuit (e.g., printed circuit board) arranged and configured as a control board for use in a geared-motor assembly in accordance with one or more features of the present disclosure.

With reference to FIG. 9, as previously mentioned, in some examples, the geared-motor assembly 400 includes a control circuit 450 arranged and configured as a control board or print-circuit board (PCB). As illustrated, the PCB may include a microcontroller 452, a wireless communication chip, a power supply 454 such as, for example, one or more batteries (e.g., coin cells), a charging circuit 456, and any other circuitry or components needed to operate the geared-motor assemblies 400 as described herein including, for example, various surface mount devices (SMD), diodes, resistors, inductors, capacitors, etc. In use, in some examples, the control circuit 450 is housed within the housing 410 adjacent to and extends (or runs) substantially parallel to the motor 430 as shown in FIG. 8.

In some examples, the control circuitry and/or PCB in each geared-motor assembly 400 may include one or more of the following components:

a microcontroller or control unit 452 arranged and configured to control, manage, etc. the various components of the geared-motor assembly 400 including activation and operation of the motor 430, communications with the external computing system, etc. In some examples, the microcontroller 452 may be a microcontroller manufactured and sold by Cypress semiconductor. The microcontroller 452 including an embedded Bluetooth (BLE) stack. In use, the microcontroller 452 is operatively coupled to the power supply 454 (e.g., battery). In some examples, the microcontroller 452 may operate at the same voltage as the battery. In some examples, the microcontroller 452 may be arranged and configured with a sleep mode to save energy usage.

a power supply 454 such as, for example, a battery. In some examples, the battery can be in the form of a flexible lithium polymer (LiPo) battery or a standard coin cell battery. By utilizing a LiPo battery, the battery can be configured to enable fast charging to restore full charge to the battery within approximately 10 minutes. In use, an external $V_{reference}$ may be incorporated to allow the voltage of the battery to be monitored. The A/D converter requires a reference to a voltage signal. Supply rails also use a voltage reference for the A/D converter.

a wireless communications transceiver such as, for example, a Bluetooth transceiver, although other forms of wireless or wired communication can be used such as, for example, a wired communication port may also be incorporated to facilitate downloading of the pre-scription plan via a hardwire connection. In some examples, the Bluetooth transceiver (e.g., Bluetooth protocol stack) may reside as firmware on the micro-controller 452. In use, the Bluetooth transceiver is arranged and configured to receive and transmit wire-less data, instructions, etc. In some examples, the housing 410 of the geared-motor assembly 400 can be manufactured from a non-metallic material since it is not directly bearing the axial load. Thus arranged, the effectiveness of the wireless communication chip and its range can be increased. In some examples, the available output current can be increased by a factor of ×1000 by manufacturing the housing from a non-metallic material and including a LiPo battery. Thus arranged, a normal BLE connection to a smart device can be incorporated without needing to use an inter-mediate hub device to ration the scarce available cur-rent.

a switch such as, for example, a reed switch. In use, the reed switch is a magnetically operated device that triggers unscheduled events via the microcontroller 452. The switch is operatively coupled to the power supply (e.g., battery) so that current can be drawn when the switch is closed. In use, the switch can be activated when the operator needs to interrupt or modify therapy.

a temperature monitoring system such as, for example, a thermistor circuit arranged and configured to monitor the temperature of the motor. For example, a Negative Temperature Coefficient (NTC) thermistor may be included. In some examples, the NTC thermistor may include a resistive element and two wires. NTC therm-istors provide thermal protection of the coil winding in the motor. In addition, NTC thermistors can be arranged and configured to monitor motor conditions such as monitor overheating, overload, and insufficient cooling of the motor. In some examples, the NTC thermistor may have a 0.1 nA quiescent current supply current draw. If the battery voltage is consumed, the same analogue to digital (A/D) value is obtained for a given temperature ensuring that the correct temperature values are obtained irrespective of the battery voltage.

a real time clock such as, for example, a real time clock (RTC) crystal may be embedded for the MCU to keep track of the current time in real time. The RTC crystal may be temperature compensated.

a bridge driver circuit may be provided to control direc-tion of travel of the motor.

a debugger unit may be provided. In use, the debugger unit is a communication interface, which serves as a point of contact for an external device to communicate with the internals of the hardware. In use, the debugger unit may communicate directly with the MCU using, for example, the pads on the PCB eliminating the need for any physical connector taking up valuable space on the PCB.

a position sensor arranged and configured to monitor absolute strut length. In some examples, the position sensor can be located on the motor to determine the overall position of the strut. In use, the sensor could be any suitable sensor such as, for example, an optical encoder or a Hall effect sensor. An optical encoder can offer higher resolution and higher accuracy compared to a magnetic encoder. In some examples, an optical encoder may include an LED light source and photo-detectors located on opposing sides of an encoder disk made of glass or plastic. By maintaining strut position in non-volatile memory this relative indication of angu-lar position may be interpreted as absolute angular position throughout the therapy period. A Hall-effect or magneto-resistive sensor measures the change in mag-net flux as the magnetic poles move relative to the sensor. The magnetic encoder is rugged and copes very well with shock and vibration, while being unaffected by the ingress of oil, dirt, and moisture. On the down-side, they are susceptible to magnetic interference caused by motors and have a limited viable operating temperature range.

one or more infrared (IR) line tracking sensors arranged and configured to confirm strut position using, for example, a distal optical encoder that tracks actual movement of the strut. In use, the encoder can be configured to verify actual travel of the strut at discrete daily intervals in order to verify that rotational move-ment of the motor has been reliably converted to linear travel of the strut. IR line tracking sensors may be configured as a peripheral low resolution encoder cir-cuit including an IR LED and a photodiode. The two line detectors may be located at the end of the geared-motor assembly. In use, the detectors consume zero power unless activated, i.e., the motor is on and actu-ating the strut, when it will take a measurement to determine the strut length.

a load sensor or accelerometer arranged and configured to provide biomechanical feedback during the correction and consolidation phases. In use, the load sensor or accelerometer can be used to determine biomechanical parameters related to (a) healing status through quan-tifying load sharing between the bone and implant, (b) pin tract loosening at the bone-implant interface, (c) distraction forces to confirm impact of automatic dis-traction, and (d) bone resistance to allow the system to "self-adjust" its distraction rate/rhythm according to the local bone environment.

an acoustic emission or vibration sensor arranged and configured to provide fault level detection in the gear train. In use, the acoustic emission or vibration sensor can detect faults in the event that the pinion gears become misaligned during re-attachment of the gear motor after X-ray or showering by the patient.

a charge pump arranged and configured as a DC to DC converter. In some examples, the charge pump may utilize capacitors for energetic charge storage to raise or lower voltage. In some examples, the charge pumps may be used for the encoder and the motor. In some examples, the charge pumps may be used for gate-driving high-side n-channel power MOSFETs and IGBTs. In use, when the center of a half bridge goes low, the capacitor may be charged through a diode, and this charge may be used to later drive the gate of the high-side FET a few volts above the source voltage so as to switch it on.

an encoder voltage translator may be utilized to read the encoder output using two Metal Oxide Semiconductor Field Effect Transistors (MOSFET's). In some examples, power may be supplied on one side directly by the battery and by the encoder supply on the other side. This allows the logic to be transferred to the MCU. The MOSFET voltage translators prevent damage to the processor pins at higher voltages than the battery.

a motor charge pump may be utilized to convert 3V to 20V and is responsible for driving the motor. In use, the 20V need not be a "steady state" 20V rather building up 20V on the capacitor ensures that it can be released as a "pulse" to the motor. It can be released as a pulse in two directions, i.e., the motor can operate in anti-clockwise "retract" or clockwise "extend" directions.

a capacitor voltage measurement system may be utilized, the system including three low current switches rated at 100 pA, which can measure the voltage on the capacitor before and after it has delivered a pulse to the motor. By selecting the appropriate current switch and MOSFET circuit to short-circuit, the burst of current can be forced through the motor in two different directions. The duration of the pulse is controlled with PWM signals from the two MOSFET's (anti-clockwise or clockwise). The pulse is long enough to drive the motor for the distance required. In use, the change in voltage across the capacitor tell us the energy delivered to the motor, which can be indirectly linked to the torque on the motor.

a motor drive circuit can be utilized, the circuit arranged and configured to drive the motor using a capacitor charge-discharge circuit to monitor the load on the motor on each motor pulse.

Figure 10:
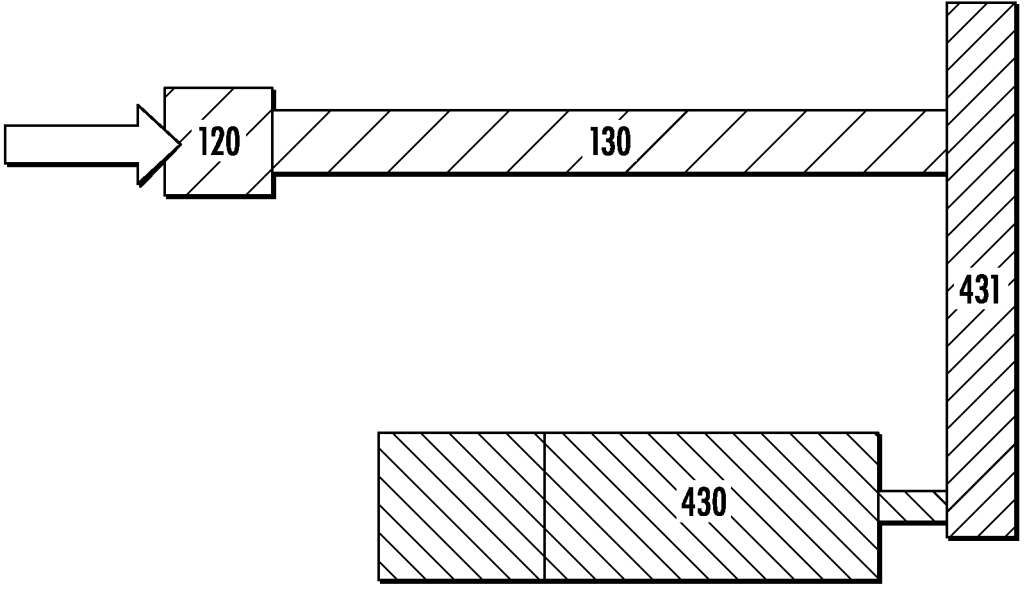
FIG. 10 illustrates a schematic representation of the offset motor design in accordance with one or more features of the present disclosure, the motor being coupled to the threaded rod of the strut via a torque transmitting mechanism (e.g., transmission, gears, etc.)

As previously mentioned, when coupled to the strut 106, the geared-motor assembly 400 presents an offset design wherein the longitudinal axis of the motor 430 and the output shaft 434 are offset, or spaced a distance from, the longitudinal axis of the threaded rod 130 and the strut 106, as generally illustrated in FIG. 10. As such, the geared-motor assembly 400 uses a torque transferring mechanism such as, for example, interconnected first and second gears 132, 432, for transferring rotation from the motor 430 to the strut 106. In some examples, the strut incorporating the geared-motor assembly is arranged and configured to achieve a target axial compression force of 1000N, which represents the antici-pated worst case clinical loading scenario, e.g., during a stumble, walking up and down the stairs, or from asymmetrical loading across the frame. By utilizing an offset design, the motor can be isolated from any axial load it might be subjected too. Further, incorporation of additional gear reduction from spur gears can provide additional protection to the "in-line" integrated gearbox. That is, for example, a secondary reduction gear could be used to protect the integrated gearbox from excessive damage due to over-loading during a scheduled adjustment, which could occur during patient activity. In some examples, adding a 3:1 gear reduction following the motor gearbox would increase the compression force resistance to 660N.

When utilizing offset designs, proper installation and alignment of the gears is needed, which can be difficult without some type of feedback. Misalignments in gears can cause vibration, premature wear, and contact nonlinearities, which in turn may cause load distribution shift on the gear tooth. The load distribution shift of the gear pair may result in increased contact and bending stresses with the maximum stresses leaning towards the edge of the face width. These stress changes cause failures and sub-optimal gear performance.

In accordance with one or more features of the present disclosure, to maintain mesh alignment (radial, axial and angular) between the transmission gears after re-attachment of the geared motor assembly, vibration and noise based health monitoring techniques can be used to detecting anomalies in the time domain and frequency domain (e.g., using Fast Fourier Transform analysis). This approach may utilize acoustic emission (AE) sensors for fault detection and diagnosis. When there is a force variation in a gearbox, the component will generate a vibration. This vibration is then transmitted to the surrounding structure, and therefore noise and vibration will be generated in the gearbox. Vibration signal analysis is an important tool to experimentally inves-tigate gear vibration because gears generate vibrations at specific frequencies, which are related to the number of gear teeth and the rotational speed of the gear shaft. AE signals are relatively unaffected by structural resonance and are more sensitive to early fault activities than vibrational sensors. AE emitted by very small defects occurs in fre-quency ranges that are higher than the operational ranges of vibration sensors and therefore might not be caught by vibration sensors. Furthermore, if there is only a small crack or surface wear in the pinion gears, it may not be severe enough to change the structural vibration. Vibration signals collected by accelerometers, which measures the second derivative of the displacement, may still remain the same, and thus be unable to detect the incipient fault.

Figure 11:
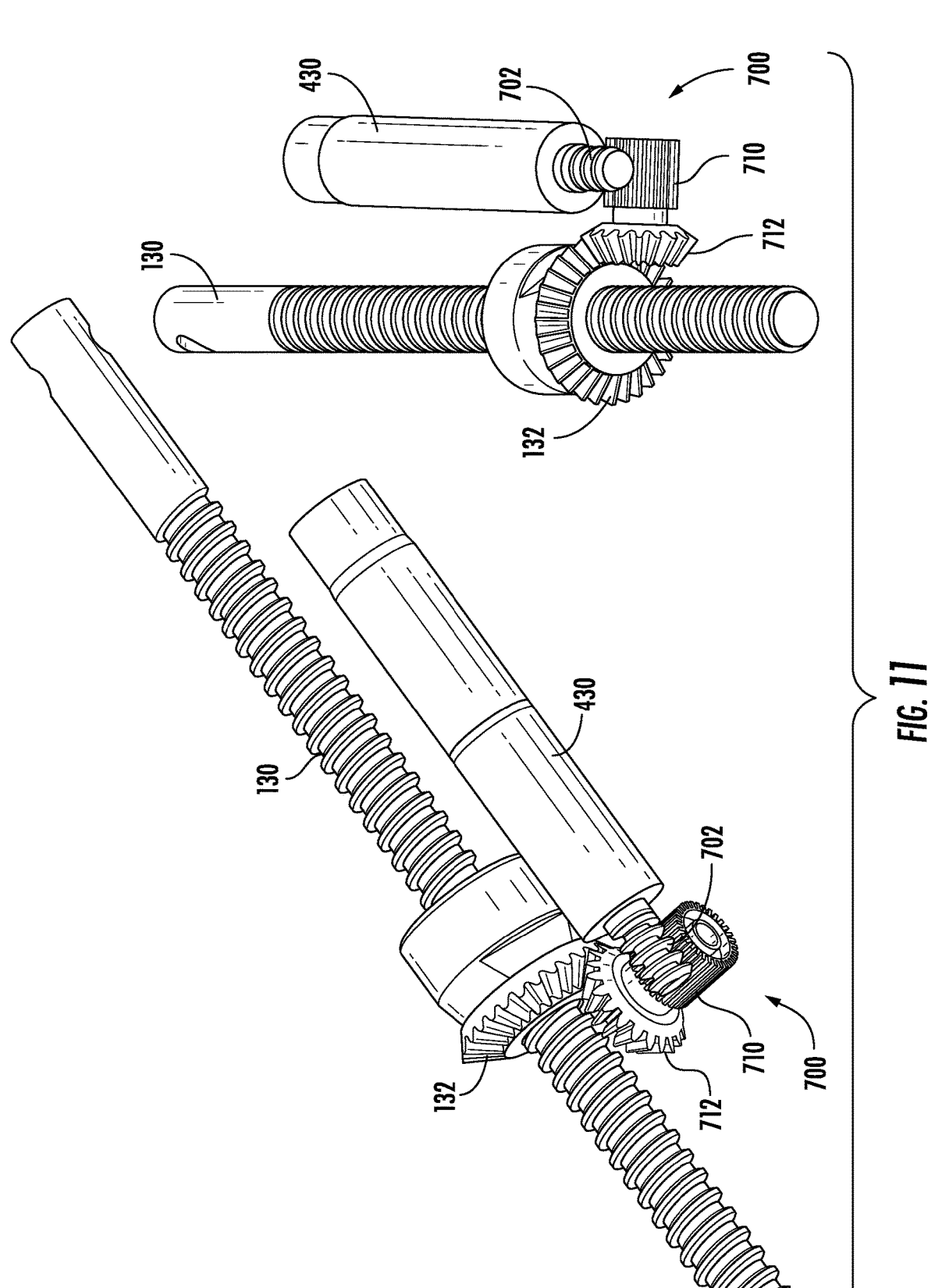
FIG. 11 illustrates various views of an alternate example of a torque transmitting mechanism in accordance with one or more features of the present disclosure.

With reference to FIG. 11, the geared-motor assembly 400 may include a worm-drive mechanism or transmission 700 to couple the output shaft 434 of the motor 430 to the threaded rod 130 of the strut 106. As illustrated, in some examples, the output shaft 434 of the motor 430 can include, or be formed in, a worm drive 702 having, for example, a 5 mm diameter and a 1 mm pitch. The worm drive 702 being coupled to an intermediate shaft 710 at a first end thereof. The second end of the intermediate shaft 710 including a gear 712 for coupling to a gear 132 on the threaded rod 130, as will be described in greater detail below. In some examples, by utilizing a worm-drive mechanism or trans-mission 700 to couple the motor 430 to the threaded rod 130 a reduction ratio of 30:1 can be achieved resulting in compression force resistance of several thousand Newtons. For example, when utilizing a threaded rod 130 having a 1.0 mm pitch, the range of torque to drive a 1000N linear load would increase from 614 mNm to 921 mNm depending on the coefficient of friction (0.15 to 0.25). If the two contacting materials were stainless steel and aluminum then the coef-ficient of friction would increase to 0.6 for the static case, which would predict a torque requirement of 2000 mNm for a 1000N linear load. Static is more relevant than dynamic because most of the time the threaded rod of the strut is non-moving and the motor will need to be able to overcome the static resistive force. This would require a reduction gear assembly of at least 13:1. By utilizing a worm-drive mecha-nism or transmission 700 to drive a gear 132 such as, for example, a spur gear, on the threaded rod 130 of the strut 106, the worm-drive mechanism or transmission 700 can achieve a reduction ratio of 30:1 increasing the compression force resistance to several thousand Newtons. As such, utilization of the worm-gear drive mechanism or transmis-sion 700 to drive the spur gear that is used to engage the threaded rod 130 of the strut 106 improves the performance of the motor.

In some examples, as illustrated, the gear 132 coupled to the threaded rod 130 of the strut 106 and the gear 712 at the second end of the intermediate shaft 710 could be provided in the form of bevel gears, rather than spur gears (e.g., straight gears), so that the offset interface gears coupling the output shaft 434 of the motor 430 to the threaded rod 130 rotate at right-angles to the threaded rod. Thus arranged, in use, the offset interface gears can be driven by the worm-gear mechanism in preference to a standard pinion gear arrangement thus enabling a reduction of 13:1 to be achieved from the motor 430 to the gear 132 of the threaded rod 130. In use, the illustrated example utilizing worm gears achieves a gear reduction ratio of 30:1 because the worm drive is driving 15 teeth, i.e., 15 revolutions of the worm drive means 1 revolution of the gear) and the beveled gears have a 2:1 ratio, which means a total reduction of 30:1. Utilizing a 10 mm diameter Portescap geared stepper motor can provide a torque rating of 150 mNm. Therefore, this overall arrangement could comfortably support 2000 mNm even allowing for efficiency losses, and deliver 1000N linear force using the existing threaded rod of the strut.

In addition, and/or alternatively, in some examples, by switching to a duty cycle from an adjustment once every minute to once every 45 seconds, which would increase the number of adjustment intervals from 1440 to 1920 adjustment intervals per day, respectively, a 33% increase in adjustment intervals could accommodate any attempt made by the software to adjust the spatial frame during very high loading periods allowing the system to skip and make adjustments at the next interval. This type of duty cycle would ensure that strut adjustments were only attempted when the applied forces are light, whilst still maintaining a more fractionated rhythm for bone adjustment.

Thus arranged, in accordance with one or more features of the present disclosure, a selectively attachable and detachable geared-motor assembly 400 is disclosed. In use, with the geared-motor assembly 400 detached, the struts 106 can be manually adjusted (e.g., rotated). For example, it is envisioned that the struts 106 can be manually adjusted to their necessary starting position in the operating room by a health care provider (e.g., surgeon) to facilitate initial setup and construction of the spatial frame. By enabling the geared-motor assemblies 400 to be easily detachable, the initial length of the strut 106 can be easily set up by conventional processes. Thereafter, after completion or construction of the spatial frame, the geared-motor assemblies 400 can be coupled to the struts 106. For example, the geared-motor assemblies 400 can be coupled to each of the plurality of struts 106 in clinic to enable subsequent automated and/or motorized adjusts to the length of the struts as required by the treatment plan, although it is envisioned that the geared-motor assemblies could be coupled to the struts at any point during treatment. By configuring the geared-motor assemblies 400 to be coupled to the manually adjustable struts 106 in a fracture clinic once the spatial frame has been surgically attached onto the patient, the need for sterilization of the geared-motor assemblies 400 is eliminated thereby facilitating easier assembling and maintenance of the geared-motor assemblies 400.

Figure 12A:
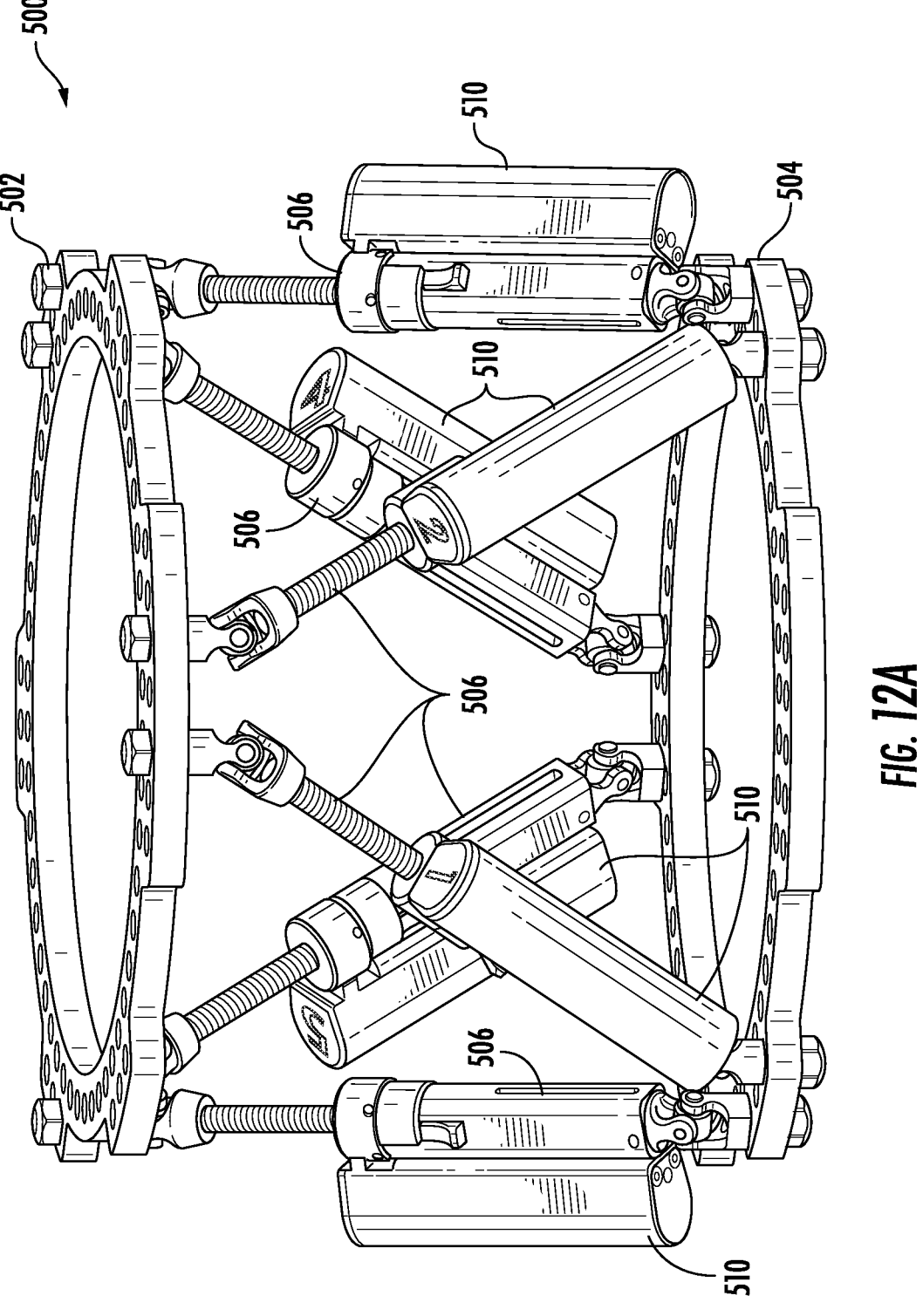
FIG. 12A illustrates a perspective view of an alternate example of a spatial frame including a plurality of geared-motor assemblies coupled to a plurality of struts, respectively, in accordance with one or more features of the present disclosure.

In accordance with one or more features of the present disclosure, with reference to FIGS. 12A-12Q, an exemplary spatial frame 500 is disclosed. As illustrated, the spatial frame 500 may include first and second platforms 502, 504 and a plurality of struts 506 coupled thereto. In use, each of the plurality of struts 506 is arranged and configured to receive, couple to, mate with, etc. a geared-motor assembly 510. As will be appreciated by one of ordinary skill in the art, the geared-motor assembly 510 may be similar in operation and configuration to the previously described geared-motor assemblies described herein except as provided for below.

In accordance with one or more features of the present disclosure, and as previously described, each geared-motor assembly 510 may be arranged and configured as a self-contained unit including any necessary components required for operation including, for example, powered electronics including any control circuit or printed-circuit board (PCB) 511, microprocessor, wireless communication chip(s), wireless transmitter(s), wireless receiver(s), antenna(s), power supply (e.g., one or more batteries) 515, and motor 514 such as, for example, exemplary PCB 450, microprocessor 452, power supply 454, and motor previously described herein. Thus arranged, each geared-motor assembly 510 is arranged and configured to operate as a stand-alone device without the need for any wires for coupling to, for example, a central controller and/or a main power supply coupled to, for example, one of the first or second platforms. Each geared-motor assembly 510 is arranged and configured with all of the intelligence needed to control the strut 506 to which it is attached along with any needed power supply for suppling power to the microprocessor, PCB, motor, etc. In addition, each geared-motor assembly 510 may be arranged and configured to receive and/or transmit data, instructions, etc. with a remote computing device or external computing device (e.g., a central computer, a mobile device, etc.), with other geared-motor assemblies 510, etc. Thus arranged, each geared-motor assembly 510 may be arranged and configured to receive instructions from, for example, a mobile device, another geared-motor assembly 510, etc. and to control (e.g., extend, retract, etc.) the strut 506 to which it is coupled based on said instructions.

In accordance with one or more features of the present disclosure, in some examples, one of the plurality of motor-geared assemblies 510 may be configured as a primary assembly, which is arranged and configured to communicate with the remote computing device, as well as remaining motor-geared assemblies 510, which may be configured as secondary assemblies. In use, the primary assembly is configured to transmit data, instructions, etc. received from the remote computing device to the other remaining secondary assemblies. In one particular example, the primary assembly may be altered, switched, transferred, etc. during use of the spatial frame 500 (e.g., the primary assembly may be selectively interchangeable such that responsibilities associated with the primary assembly can be transferred to one of the secondary assemblies). In use, each geared-motor assembly 510 may include software programed to selectively transfer responsibilities of the primary assembly. For example, the primary assembly may be altered, switched, transferred, etc. to one of the secondary assemblies depending on, for example, remaining power supply. Thus, for example, if the system determines that the designated primary assembly has a lower remaining power supply than the other secondary assemblies, the responsibilities of the primary assembly may be transferred to one of the secondary assemblies such as, for example, the secondary assembly with the largest remaining power supply. That is, for example, in use, the primary assembly may be arranged and configured to communicate with an APP running on a user's smartphone. During use, it is envisioned that the largest power supply requirement may be needed for communication with the APP. As such, during use, it is envisioned that the power supply of the primary assembly may drain faster than the remaining secondary assemblies. In an effort to prevent the power supply of the primary assembly from draining before the power supply of the remaining secondary assemblies, responsibilities of the primary assembly may be transferred to one of the other secondary assemblies depending on, for example, remaining power supply. Alternatively, or in addition, responsibilities associated with the primary assembly may be transferred to one of the secondary assemblies when a remaining power supply level of the primary assembly is below a threshold value. Alternatively, or in addition, responsibilities associated with the primary assembly may be transferred to one of the secondary assemblies based on which assembly has the most/least remaining adjustments, via a calendar or schedule, (e.g., a predetermined schedule), etc. Alternatively, in some examples, each geared-motor assembly may be arranged and configured to communicate directly with the remote computing device (e.g., APP running on a user's smartphone).

As previously mentioned, in use, the geared-motor assembly 510 may be coupled to a strut 506 by any suitable coupling mechanism now known or hereafter developed. In accordance with one or more additional features of the present disclosure, each strut 506 may include a housing 530 and a gear 532 coupled to the threaded rod 534 of the strut 506, the gear 532 may be positioned within the housing 530 of the strut 506. In addition, the housing 530 may include an opening 540 for providing access to the gear 532. The housing 530 may also include one or more recesses 542 for engaging one or more projections, feet, pegs, etc. For example, as illustrated, the housing 530 may include first, second, and third recesses 542A, 542B, 542C for engaging first and second projections or feet 524A, 524B and a spring-loaded projection or peg 526 extending from the geared-motor assembly 510 as will be described in greater detail below, although this is but one configuration and more or less projections or feet may be utilized. Moreover, as will be described in greater detail below, the geared-motor assemblies 510 and/or the strut 506 may include one or more mechanisms for facilitating disengagement of the geared motor assemblies 510 from the strut 506. For example, with reference to FIG. 12G, the housing 530 of the strut 506 may include a removal hole 544 in communication with the third recess 542C, the removal hole 544 arranged and configured to enable access to the spring-loaded projection or peg 526 to permit one to disengage the geared-motor assembly 510 from the strut 506 as needed, although this is but one configuration or mechanism and others are envisioned such as, for example, utilization of a lever as will be shown and described below.

Figures 12B, 12C:
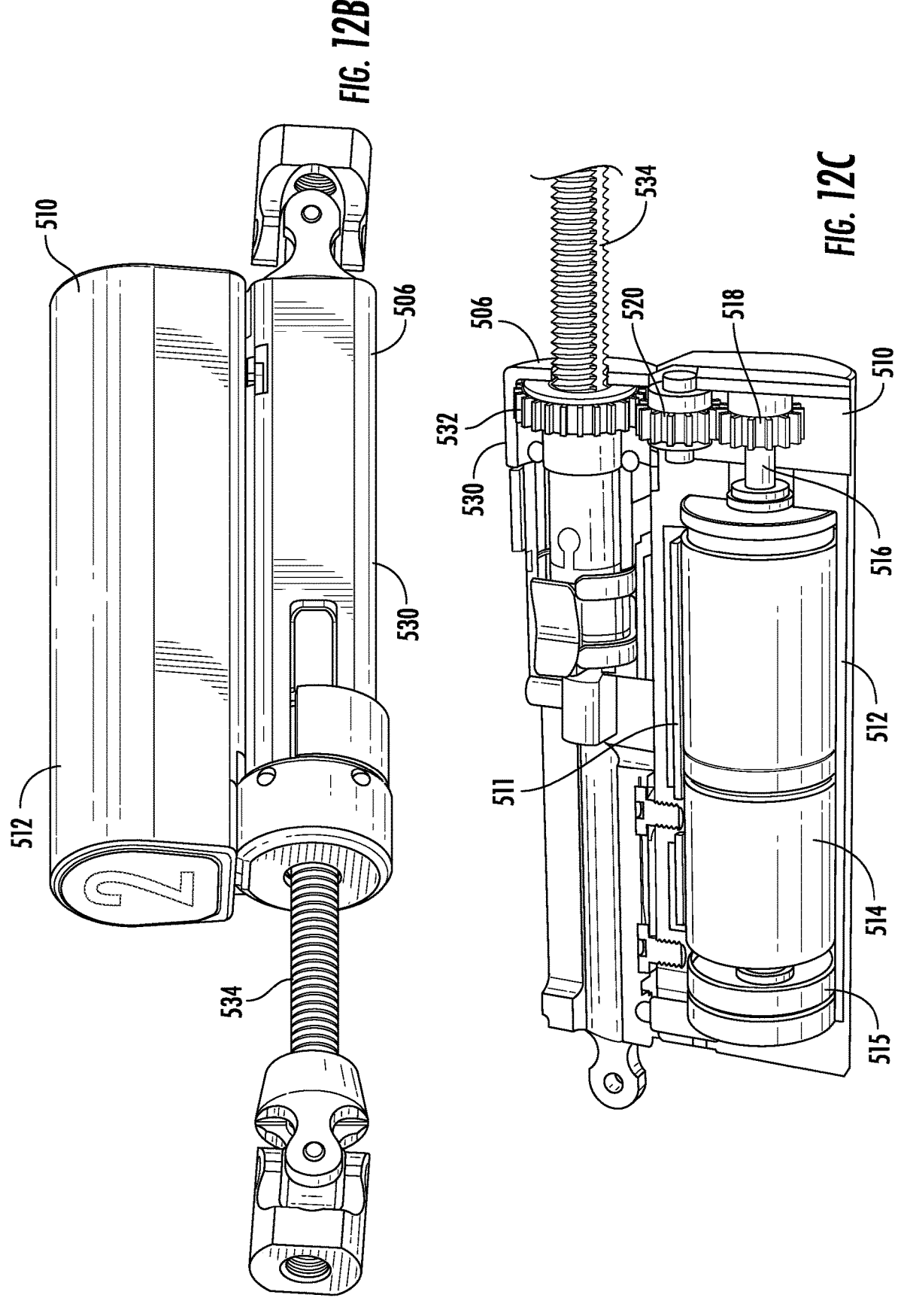
FIG. 12B illustrates a side perspective view of the geared-motor assembly and strut shown in FIG. 12A.
FIG. 12C illustrates a perspective view of the geared-motor assembly and strut shown in FIG. 12A, portions of the housings removed.

As illustrated, each of the geared motor assemblies 510 may include a housing 512 and a motor 514 including an output shaft 516 and a gear 518. In use, the gear 518 associated with the motor 514 may be directly coupled to the gear 532 associated with the strut 506. Alternatively, as illustrated in FIG. 12C, the geared-motor assembly 510 may include one or more intermediate or idlers gears such as, for example, an intermediate or idler gear 520, arranged and configured to interact with the gear 518 of the motor 514 and the gear 532 of the strut 506. As will be appreciated by one of ordinary skill in the art, incorporation of one or more intermediate or idler gears 520 enables a smaller diameter motor gear 518 and/or gear-reduction. In addition, as previously described, each geared-motor assembly 510 may include any additional components, sensors, etc. needed for operation.

Figures 12D, 12E:
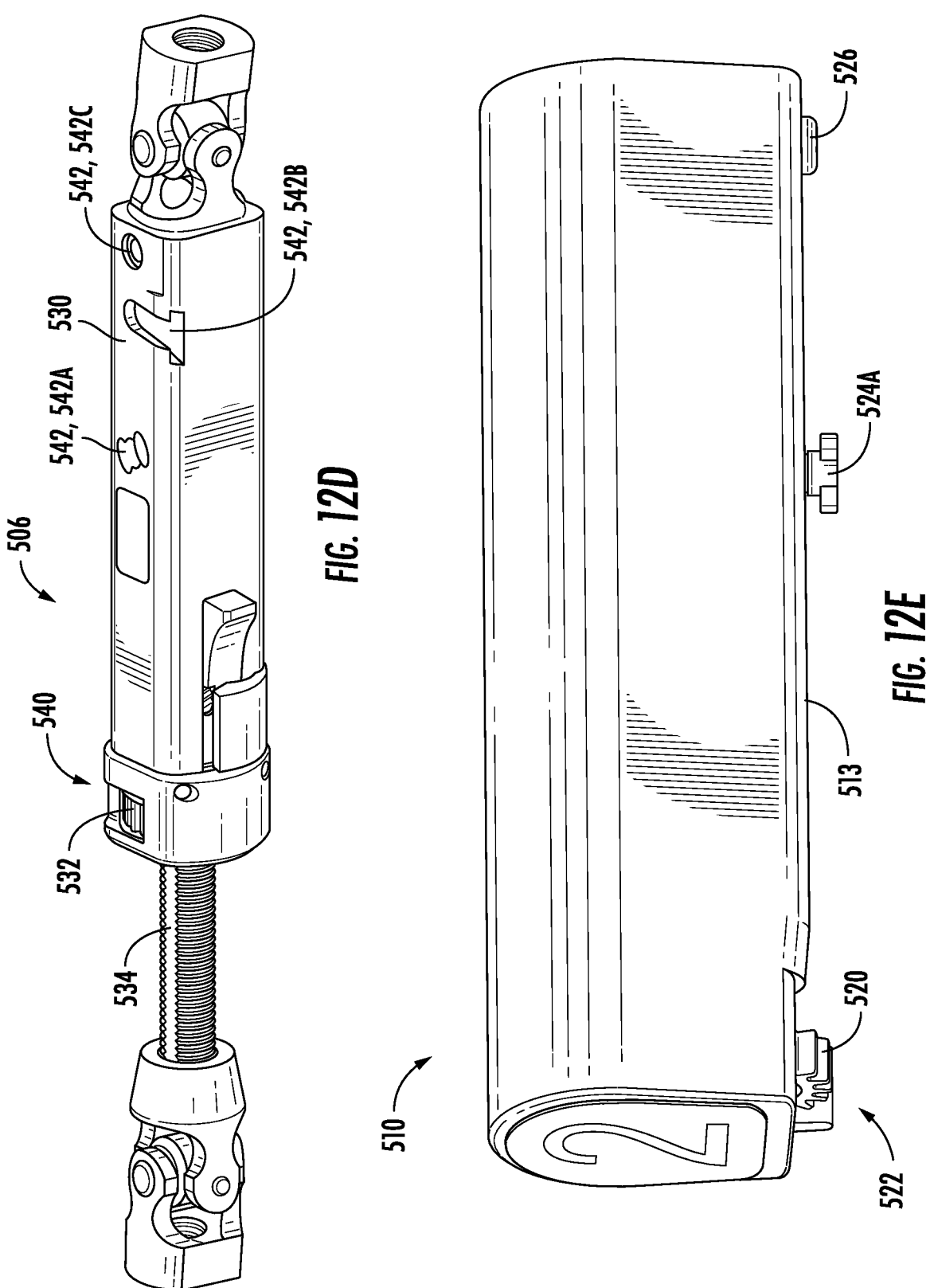
FIG. 12D illustrates a perspective view of the strut shown in FIG. 12A.
FIG. 12E illustrates a perspective view of the geared-motor assembly shown in FIG. 12A.
Figure 12F:
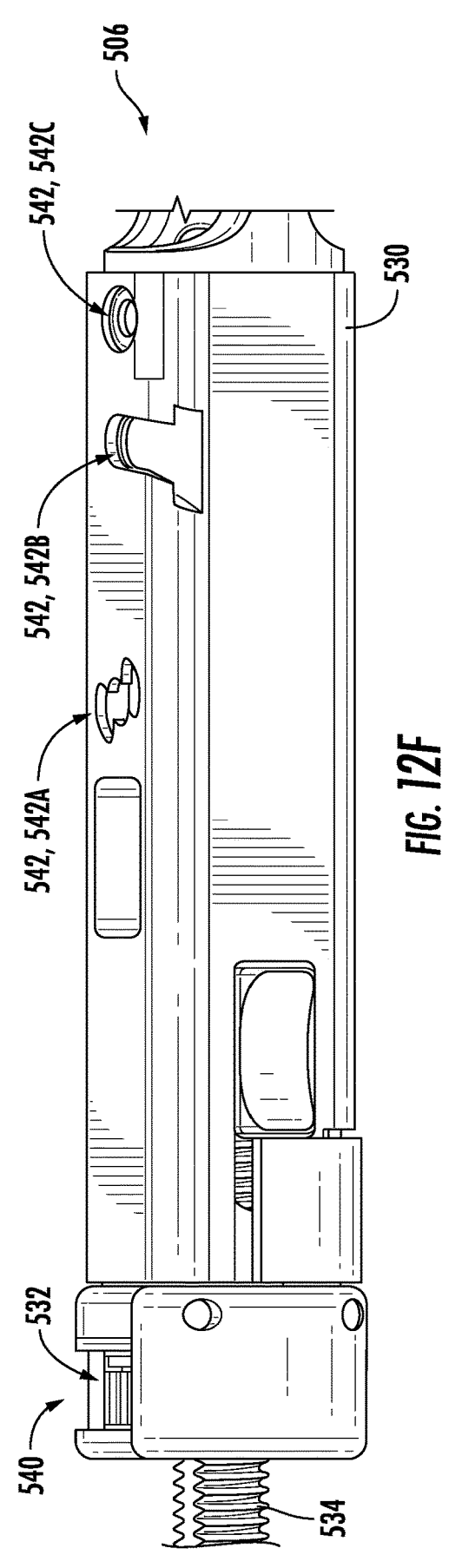
FIG. 12F illustrates a perspective view of the strut shown in FIG. 12A.

In accordance with one or more features of the present disclosure, the housing 512 of the geared-motor assembly 510 may include an opening 522 arranged and configured to enable access to the gear(s) 518, 520 associated with the motor 514. For example, as illustrate in FIG. 12E, if included access to the intermediate or idler gear 520, alternatively, access to the gear 518 of the motor 514 may be provided (e.g., gear 518 or gear 520 may protrude from the housing 512 of the geared-motor assembly 510 to engage, mesh, etc. with the gear 532 of the strut 506). In addition, the housing 512 of the geared-motor assembly 510 may include first and second projections or feet 524A, 524B and a spring-loaded projection or peg 526 for facilitating coupling of the geared-motor assembly 510 to the housing 530 of the strut 506. As illustrated, in some examples, at least the first projection or foot 524A is arranged and configured with a T-shaped tip to enable rotation of the geared-motor assembly 510 relative to the housing 530 of the strut 506. In addition, incorporation of the T-shaped tip prevents the geared-motor assembly 510 from moving away from the housing 530 of the strut 506.

Alternatively, it is envisioned that the spring-loaded projection or peg 526 may be incorporated with, into, etc. with the second projection or foot 524B. Thus arranged, the need for two projections or feet and a spring-loaded peg along with first, second, and third corresponding recesses may be eliminated thereby enabling a shorter minimum length by negating the need for the third recess on the strut side. As such, for clarity, the recess arranged and configured to receive the spring-loaded peg may also be referred to as a peg recess).

With reference to FIGS. 12J-12Q, each of the geared-motor assemblies 510 may be coupled to each of the struts 506 by aligning the first projection or foot 524A extending from the housing 512 of the geared-motor assembly 510 with the first recess 542A formed in the housing 530 of the strut 506. As illustrated, during alignment, the geared-motor assembly 510 is positioned at an angle relative to the housing 530 of the strut 506.

Next, the geared-motor assembly 510 is advanced toward the housing 530 of the strut 506 until the bottom surface 513 of the housing 512 of the geared-motor assembly 510 (e.g., flat, bottom surface 513 of the housing 512 of the geared-motor assembly 510) contacts the surface of the housing 530 of the strut 506. At this point, the first projection or foot 524A extending from the housing 512 of the geared-motor assembly 510 should be positioned within (e.g., seated) within the first recess 542A formed in the housing 530 of the strut 506.

Next, the geared-motor assembly 510 may be rotated relative to the housing 530 of the strut 506. The geared-motor assembly 510 is rotated until the second projection or foot 524B extending from the housing 512 of the geared-motor assembly 510 mates with the second recess 542B formed in the housing 530 of the strut 506. At this point, the spring-loaded projection or peg 526 begins to be pressed up away from the housing 530 of the strut 506 as it contacts and rides up a ramp feature formed on the on the housing 530 of the strut 506. The geared-motor assembly 510 is rotated until the spring-loaded projection or peg 526 aligns with the third recess 542C formed in the housing 530 of the strut 506. Once properly aligned, the spring-loaded projection or peg 526 extends (e.g., drops) into the third recess 542C securing the geared-motor assembly 510 in its final, locked position. In its final, locked position, the geared-motor assembly 510 is securely coupled to the housing 530 of the strut 506 with the gears 518, 520, 532 intermeshed. An optional set screw 550 (FIG. 12I) may be installed to securely lock the position of the geared-motor assembly 510 to the housing 530 of the strut 506.

Figure 12G:
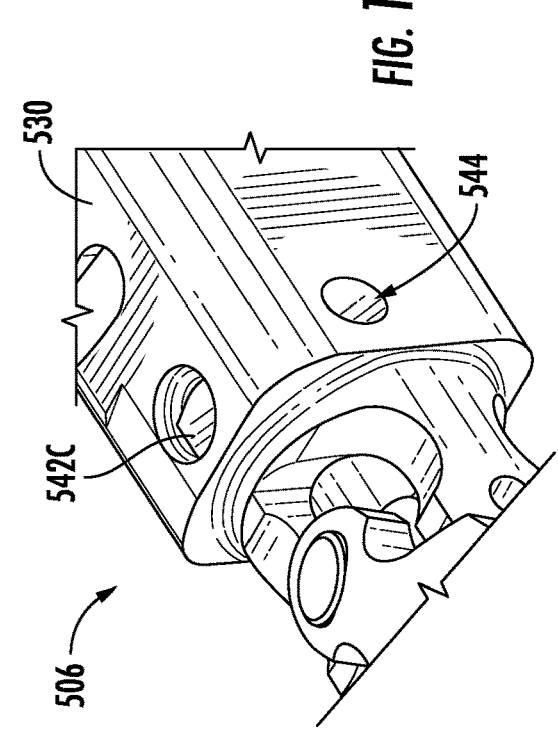
FIG. 12G illustrates a detailed, perspective view of the strut shown in FIG. 12A.
Figures 12H, 12I:
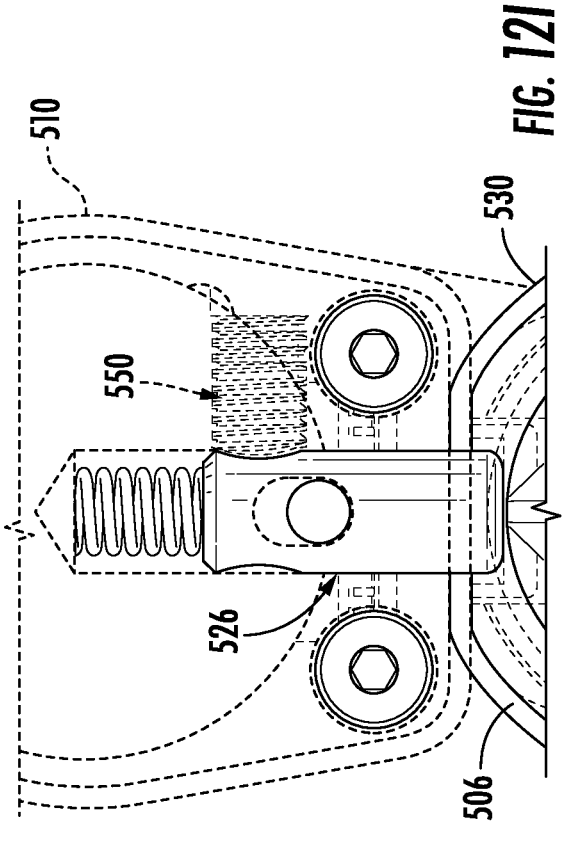
FIG. 12H illustrates a bottom view of the geared-motor assembly shown in FIG. 12A.
FIG. 12I illustrates a cross-sectional view of the geared-motor assembly shown in FIG. 12A.
Figures 12J, 12K:
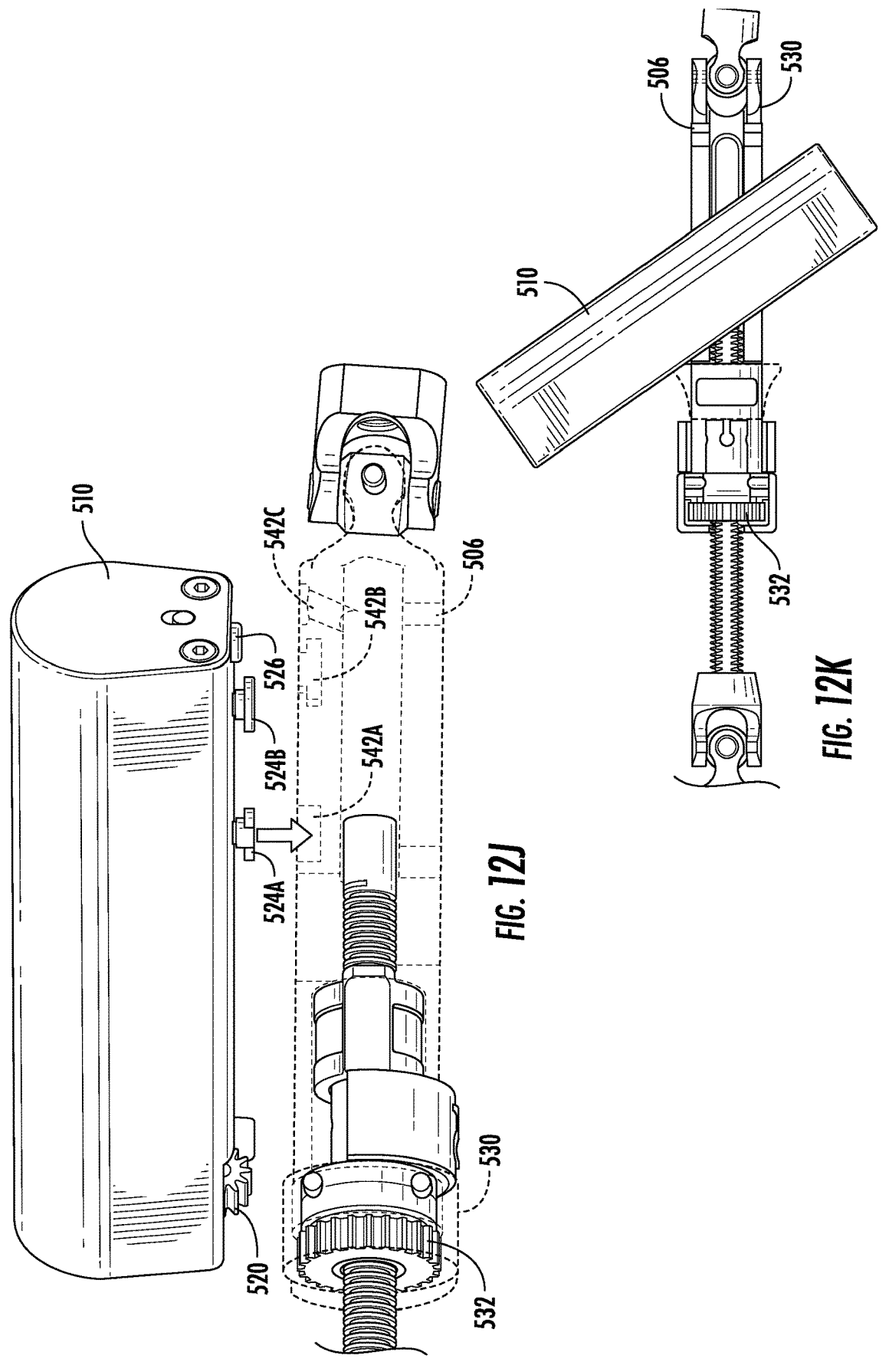
Figure 12N:
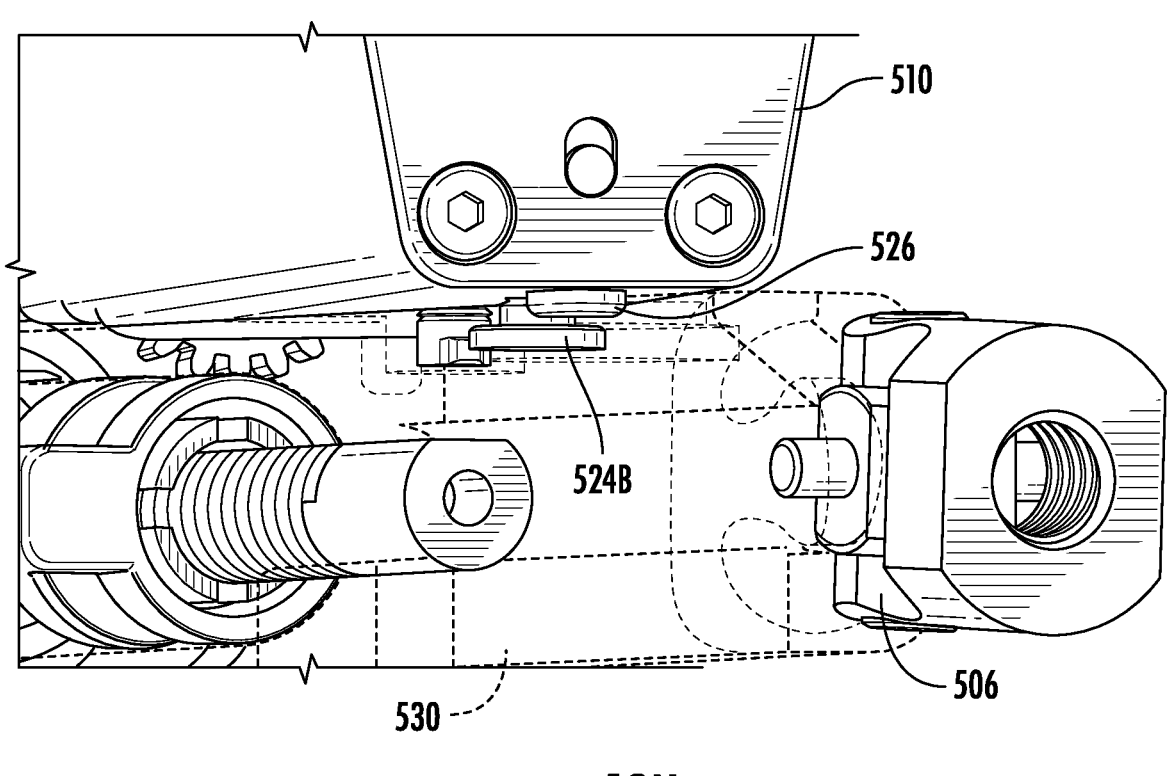
Figure 12O:
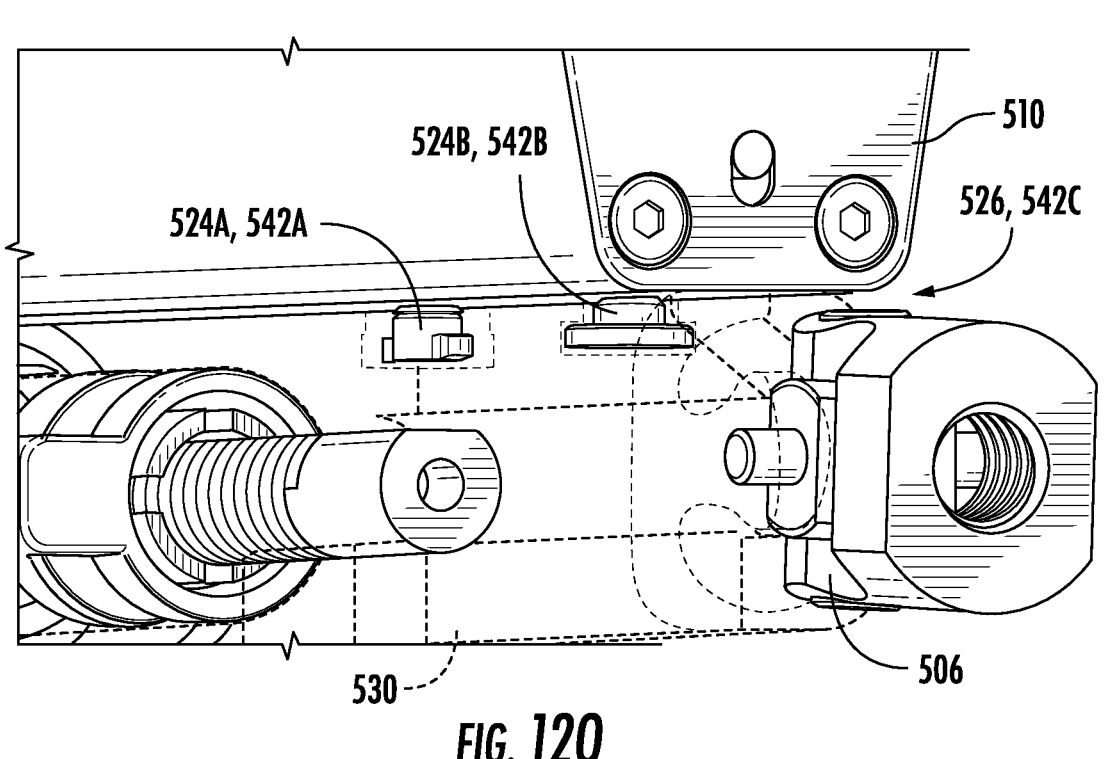
Figure 13A:
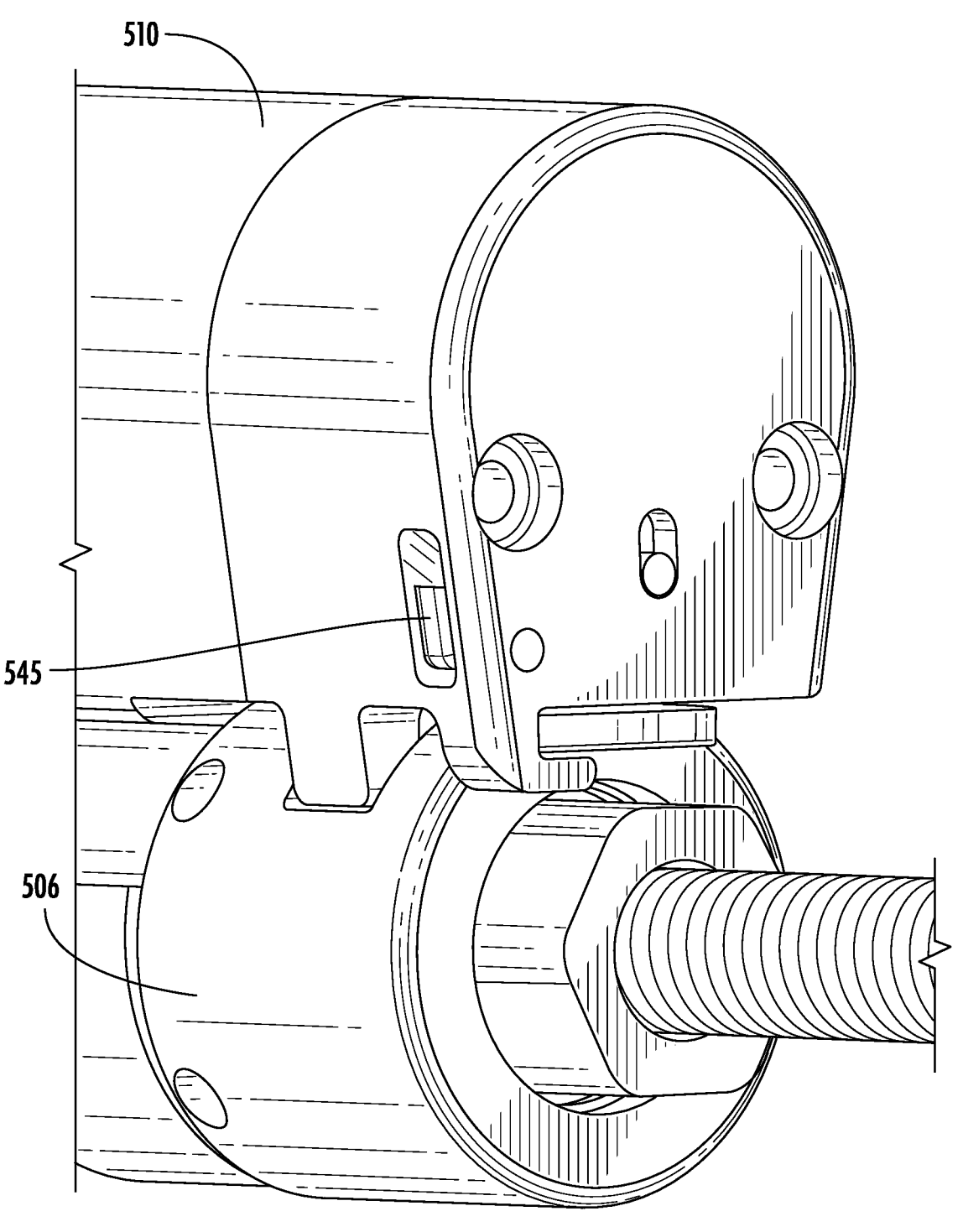
FIGS. 13A and 13B illustrate various views of an alternate example of a mechanism to facilitate disengagement of a geared-motor assembly from a strut in accordance with one or more features of the present disclosure.
Figure 13B:
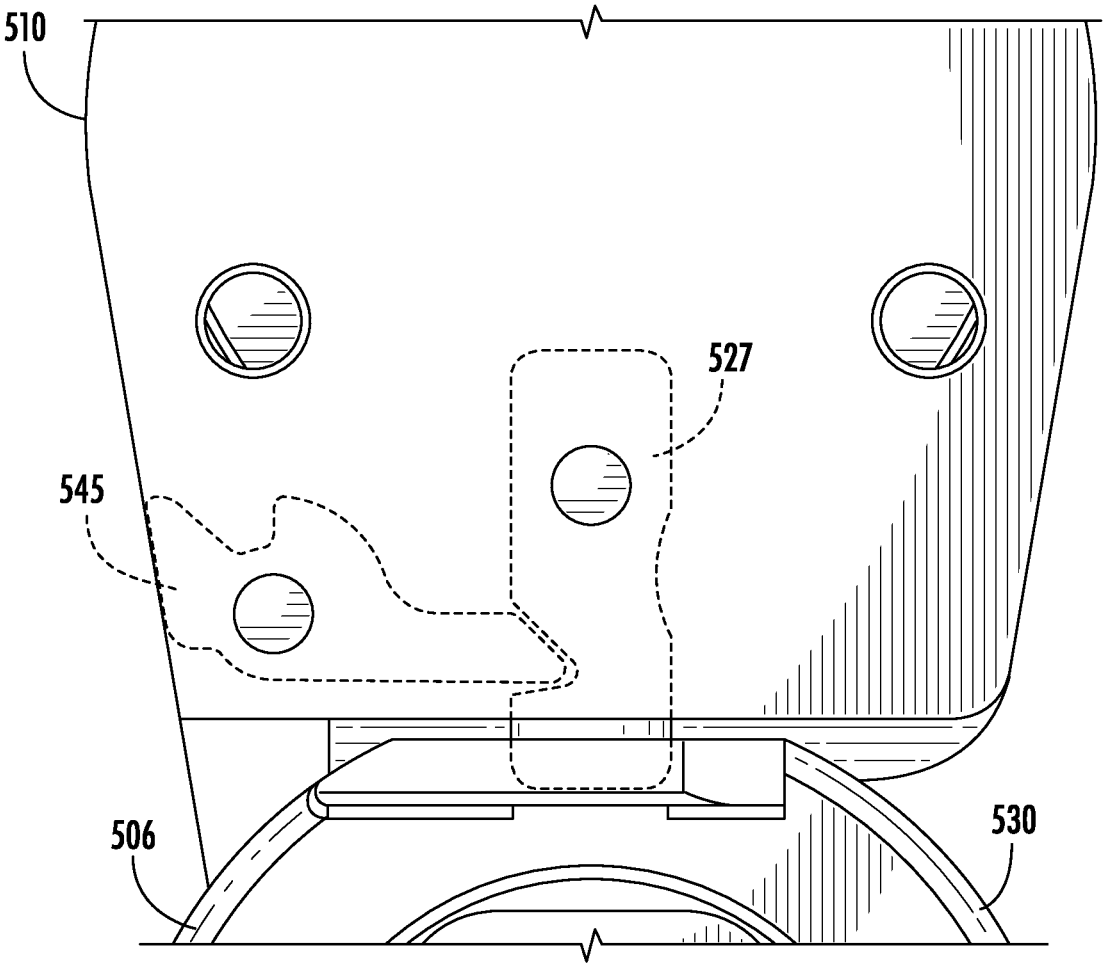

With reference to FIG. 12G, the housing 530 of the strut 506 may include a removal hole 544 arranged and configured to receive a tool. In use, the tool may be inserted into the removal hole 544 and into contact with the spring-loaded projection or peg 526. Thus arranged, the tool can be used to push up on the spring-loaded projection or peg 526 allowing for removal of the projection or peg 526 from the third recess 542C (e.g., allows projection or peg 526 to be pushed out of the third recess 542C against the bias of the spring) and thus allowing the geared-motor assembly 510 to be rotated relative to the housing 530 of the strut 506 and thus enabling disengagement of the geared-motor assembly 510 from the housing 530 of the strut 506. However, as previously mentioned, the geared-motor assemblies 510 and/or the strut 506 may include any other suitable mechanism to facilitate disengagement of the geared motor assemblies 510 from the strut 506. For example, with reference to FIGS. 13A and 13B, the geared-motor assemblies 510 may include a lever 545 arranged and configured to engage, for example, the spring loaded-peg 526 or other projection 527 extending from the strut 506. In use, to disengage the geared-motor assembly 510 from the strut 506, the user can activate the lever 545 thereby disengaging the peg 526 or other projection 527, and thus the geared-motor assembly 510 from the strut 506.

Thus arranged, in use, each of the geared-motor assemblies 510 can be coupled to the housing 530 of a strut 506 without the use of any additional tools. In use, the incorporation of the projections or feet 524A, 524B enable control location and height of the geared-motor assembly 510. The spring-loaded projection or peg 526 seats to lock the position of the geared-motor assembly 510 relative to the housing 530 of the strut 506. Intermeshing gears 520, 532 of the strut 506 and motor 514 roll into engagement when attached, which prevents peak or tips of the gears from contacting each other, which minimizes potential for interference during meshing of the gears. If needed, the geared-motor assembly 510 can be removed by utilizing a small diameter tool to contact the spring-loaded projection or peg 526.

As discussed above, the spatial frame 500, and in particular, its geared-motor assemblies 510 may be configured to wirelessly communicate with one another as well as with one or more external devices. To simplify such wireless communication between geared-motor assemblies 510, one of the assemblies 510 may be selected and may subsequently act as a primary assembly for the purposes of communication with one or more external devices, as well as communication and/or control other or secondary assemblies 510. The secondary assemblies 510 may be configured to communicate only with the primary assembly 510. Alternatively, or in addition, the secondary assemblies 510 may communicate with other secondary assemblies 510 and/or one or more external devices.

While having a single assembly 510 as the primary assembly for communication, control, etc. functionalities may have several technical and usability advantages, it may cause a faster power source draining of the primary assembly 510's power source than power sources of secondary assemblies 510. For example, if each assembly 510 is powered by independent batteries, the primary assembly 510's battery may run out of power faster than the secondary assemblies because of the additional power consumption required for strut communication, data analysis, etc.

Moreover, during operation (e.g., strut adjustments), each assembly 510 might not experience the same loading or any other operational conditions. For example, some assemblies 510 may have to overcome higher loads than others during adjustments. Different assemblies may also adjust more frequently and/or a further distance than others. Further, the loading conditions and/or prescribed adjustments of each assembly relative to other assemblies may change throughout the prescribed course of treatment. Such varying load conditions, prescribed adjustments, different length and/or frequency of adjustments, etc. of each assembly 510 may drain power source capacities differently for each assembly, such that some assemblies may drain their power sources faster than others.

In accordance with one or more features of the present disclosure, the current subject matter may be configured to assign, re-assign, change and/or shift assignments and/or designations of primary and/or secondary roles among geared-motor assemblies 510 in the spatial frame 500 based on various factors, schedules, thresholds, etc. For example, a primary role of one assembly 510 may be transferred to another assembly 510 in the spatial frame 500 based on a determination that the current power level in the power source of the current primary assembly 510 has fallen below a predetermined threshold and thus, to avoid excessive power drainage, another assembly 510 (e.g., one with the highest current power level, least amount of load, etc.) may be selected as the new primary assembly and responsibilities of the primary assembly may be transferred to it. As such, the former primary assembly will become a secondary assembly. Such change may occur dynamically (e.g., based on power level measurements, load measurements, etc.) and/or statically (e.g., based on a pre-programmed schedule, time spent as a primary assembly, strut replacement, etc.). Further, these changes may occur automatically and/or manually (e.g., using an application operating on an external device communicatively coupled to one or more assemblies 510, etc.). The above changes may be configured to ensure proper adjustment of bone segments by the spatial frame 500 as well as prevent uneven drain of power from power sources of the geared-motor assemblies 510 (as well as conserve power in the power sources).

As discussed herein, the spatial frame 500 may be configured to execute adjustments and/or manipulations of bone segments in accordance with a prescribed schedule and/or a prescription. The prescription dictates a magnitude of each adjustment, direction of each adjustment, time of each adjustment, frequency of adjustments, etc. Adjustments may be executed using a single geared-motor assembly 510 and/or any combination of assemblies 510. The assemblies 510 may adjust to different magnitudes, different directions, different frequencies, etc. The prescription may be uploaded to the spatial frame 500 wirelessly and/or using a temporary wired connection with an external device, where, for the purposes of uploading, a single assembly 510 may be selected. The communications with the assembly 510 may be performed using one or more of its antenna(s), wireless receiver(s), wireless transmitter(s), wireless communication chip(s) and/or any other hardware/software. Selection of a specific assembly 510 may be at random and/or may be identified in the prescription plan and/or based on assembly's power levels, current operational state, load, etc. and/or any other factors.

The selected assembly 510 may also be designated as a primary assembly that may be used for further communications with one or more external devices as well as other assemblies 510 in the spatial frame 500, which may be designated as secondary assemblies. The primary assembly 510 (e.g., assembly 1 as shown in FIG. 12A) may be configured to communicate with secondary assemblies 510 (e.g., assemblies 2-6 as shown in FIG. 12A), and in particular, provide operational instructions to secondary assemblies (e.g., as identified in the prescription plan, relayed from one or more external devices, determined by the primary assembly based on received data from the secondary assemblies, etc.), obtain operational status of secondary assemblies (e.g., load level, power level, positioning coordinates (including, for example, angular position(s), length/distance moved, direction of movement, etc. of the assemblies), and/or request any other information. In accordance with one or more features of the present disclosure, the primary assembly may be configured to generate one or more requests (e.g., signals, queries, etc.) to the secondary assemblies to receive their respective status updates, battery life, position data, load data, etc. Further, the primary assembly may also be configured to execute its own adjustments as identified in the prescription and/or determined by the primary assembly based on at least one of the following: its own load data, load data and/or any other data received from one or more secondary assemblies, power levels, etc.

Moreover, the primary assembly may be configured to execute analysis of all data that it has received from secondary assemblies, information contained in the prescription plan and/or any other information, and generate one or more instructions for performing adjustments to all assemblies (including itself). The analysis may be performed dynamically, and/or based on a predetermined schedule. Alternatively, or in addition, such analysis and generation of instructions may be executed by one or more external devices based on the data received from the primary assembly, where instructions may be transmitted back to the primary assembly for relaying to secondary assemblies.

In accordance with one or more features of the present disclosure, the secondary assemblies may be configured to communicate with the primary assembly only. This may include reporting any operational data, adjustment data, load data, power level data. The reporting may be executed by the secondary assemblies in accordance with a predetermined schedule and/or dynamically (e.g., based on a specific detected load, power level, etc.) and/or based on one or more requests from the primary assembly.

In accordance with one or more features of the present disclosure, when one assembly 510 (e.g., secondary assembly) is unable to execute its prescribed and/or instructed adjustment, the remaining functional assemblies 510 may be programmed and/or instructed to hold any further adjustments until the malfunctioning assembly is restored to its proper operational status (which may be reported to the primary assembly). In particular, the primary assembly 510 may be configured to inform the functioning secondary assemblies to hold adjustments if one of them becomes inoperable. Moreover, the secondary assemblies may be configured to hold their adjustments upon detecting that the primary assembly became inoperable. Such holding of adjustments may be pre-programmed and/or determined based on detection of a malfunction of one or more assemblies. Further, in some examples, each assembly may be configured, in addition to storing pre-programmed instructions for addressing inoperability of one or more assemblies, to store instructions for its own adjustments and/or adjustments of other assemblies. This way one or more assemblies and/or group of assemblies may be configured to modify their prescribed adjustments (either based on appropriate instructions from the primary assembly and/or on their own) to address any changes in operation of the spatial frame 500.

In accordance with one or more features of the present disclosure, the primary and secondary roles assigned to the assemblies 510 in the spatial frame 500 may be assigned/reassigned from and/or between assemblies. Such assignment/re-assignment may be performed based on an analysis of data gathered from each assembly during operation (e.g., power level, load level, operation status, etc.), predetermined schedule (e.g., as outlined in the prescription plan), instructions from one or more external devices, and/or any other factors. The analysis and/or subsequent determination of assignment/re-assignment of primary/secondary roles may be performed by the current primary assembly and/or one or more external devices and/or both. In some examples, assignment/re-assignment of roles may be performed based on a secondary assembly requesting to do so, for example, as a result of its current operational status. As can be understood, assignment/re-assignment of roles may be performed based on any combination of factors, data, instructions, etc. and/or using any combination of assemblies and/or external devices, etc.

By way of a non-limiting example, one or more external devices may be configured to execute an application (e.g., a web-based application) that may be configured to generate a prescription identifying how and when each assembly 510 in the spatial frame 500 may need to execute its adjustments. The prescription may or may not identify a primary assembly for communication with the secondary assemblies and/or external device(s) and/or for controlling operations of all assemblies 510. For example, as stated above, the primary assembly may be randomly selected and/or based on data that may be available at the time of generation and/or transmission of the prescription plan to the spatial frame 500. Once identified, the primary assembly 510 (e.g., assembly 1 in FIG. 12A) may be configured to begin and subsequently continue to operational control of and/or communicate with one or more secondary assemblies (e.g., assemblies 2-6 in FIG. 12A). When assignment/re-assignment of role of primary assembly becomes necessary, the current primary assembly (e.g., assembly 1) may be configured to communicate with one or more secondary assembly (e.g., assembly 2) and initiate a transfer of the primary role to that assembly. The transfer may include extraction of various data associated with operational control of the assemblies that the current primary assembly has received (e.g., prescription plan, data received during the time that assembly was primary, etc.) and stored in its memory.

In some examples, the spatial frame may be configured to include an additional control/communications module (not shown in FIGS. 12A-Q) that may be configured to manage communications among assemblies 510 and perform transfer of primary assembly roles between assemblies. It may also be configured to communicate with one or more external devices. Alternatively, or in addition, one or more external devices, via a web application, may be configured to execute transfer of primary assembly role.

In accordance with one or more features of the present disclosure, assignment/re-assignment of primary roles may be pre-programmed/pre-planned and/or dynamically and/or in any desired combination/way. For example, for pre-programmed/pre-planned assignment/re-assignment of primary roles, transfer of primary roles may be predetermined by the web application being executed by one or more external devices communicating with one or more assemblies 510. The transfer may be pre-programmed when the initial prescription plan is generated and/or based on at least one of the following: adjustment magnitude data associated with each assembly 510, adjustment frequency associated with each assembly 510, patient's anatomy and/or type of spatial frame 500 being fitted on the patient and/or any other spatial frame input parameters, modeled and/or actual power source (e.g., battery) drain data associated with each assembly 510, one or more new and/or replaced assemblies, and/or any other factors.

The modeled power source drain may be determined and/or estimated in accordance with a specific use of the spatial frame, patient anatomy and/or characteristics, and/or any other input data. The estimation may be based on various statistical modeling that may rely on historical data related to spatial frame uses, types of fractures, patient anatomies and/or characteristics, and/or any other input data, as well as use various mathematical models, artificial intelligence processes, machine learning methods, etc. to determine expected power source drain. Moreover, if a particular assembly 510 needs to be replaced, the above determinations may also be aligned with timing of replacement, as replacing a particular assembly typically requires clinical intervention.

Alternatively, or in addition, the selection and/or assignment/re-assignment of primary assembly roles may be executed dynamically based on various data gathered during operation of the spatial frame. The data may be analyzed to determine whether new primary assembly needs to be selected for further control, communication, etc. Data may be gathered by the current primary assembly and/or the web application being executed by one or more external devices. The data may include present, past and/or expected operational status of each assembly 510, its current, past and/or expected power source level, its present, past and/or expected load level, and/or any other data. Any expected levels may be determined based on the prescription plan and/or past and/or current data. Once the data is received by the primary assembly (and/or the web application and/or a separate spatial frame control module), the data is analyzed to determine whether the primary role needs to be assigned/re-assigned to another assembly.

In accordance with one or more features of the present disclosure, assignment/re-assignment of primary role may be executed at a predetermined times, which may or may not occur based on a determination of whether a particular threshold associated with, for example, power source level, load, and/or any other operational data and/or any combination thereof, is reached. Alternatively, or in addition, assignment/re-assignment of primary role may occur independent of predetermined time once such threshold is reached (e.g., power drain threshold is reached prior to the predetermined time).

Moreover, the generated prescription plan may be configured to identify one or more predetermined complex instructions (e.g., angulate one way, then lengthen, then . . . ). Such complex instructions may be more taxing on some assemblies than others, which may trigger assignment/re-assignment of the primary role of one assembly to another assembly. This change may be determined in conjunction with any of the above pre-planned and/or dynamic determinations of when and/or whether to execute assignment/re-assignment of the primary role. Alternatively, or in addition, primary roles may be assigned/re-assigned without regard for complexity of instructions in the prescription plan.

In accordance with one or more features of the present disclosure, assignment/re-assignment of the primary role may also be based on various communication parameters. For example, communication distances, antenna orientations, type of communications (e.g., Bluetooth™, WiFi, NFC, etc.), and/or any other factors may affect power level drain of a power source and thus, may be factored into the decision of whether the primary role of a particular assembly 510 may need to be assigned/re-assigned.

The following are some non-limiting examples relating to when assignment/re-assignment of the primary role of a particular assembly 510 to another assembly 510 may be performed. The primary role may be assigned/re-assigned upon determination that the primary assembly's battery drain reaches a predetermined drain level (e.g., assuming the primary assembly had 50% battery when it took over as a primary, its primary roles may be assigned/re-assigned, when its battery level drops by 5% or 10%). Alternatively, or in addition, the primary role may be assigned/re-assigned when the primary battery percentage drops below a predetermined threshold. For instance, if the primary assembly's battery level drops below 20%, its primary role may be assigned/re-assigned to another assembly 510 (e.g., assuming any other assembly 510 has more than 20% battery life). Moreover, once all assemblies' battery levels are below a predetermined threshold, the primary role may, for example, be assigned/re-assigned to an assembly with the highest level of battery remaining.

Alternatively, or in addition, assignment/re-assignment of the primary role may be based on the particulars of the prescription plan and/or as outlined in the prescription plan. Operation of the spatial frame 500 (e.g., adjustments by each assembly, communications, etc.) requires current draws (e.g., from power sources of one or more assemblies, etc.) for the purposes of activating of motors, electronics, etc. Since the motions of each strut are determined by the generated prescription plan, the entire adjustment pattern of each strut may be known prior to and/or as soon as the prescription plan is generated. The primary role may be assigned to the assembly 510 that may be determined to adjust the least amount over the course of the prescription plan. This may allow to preserve as much power in that assembly's power source as possible. Similarly, the primary role may be assigned to the assembly which may adjust the least amount during an initial period (as, for example, defined by the prescription plan and/or determined based on the plan, specific spatial frame, type of fracture, and/or any other factors) and be assigned/re-assigned any number of times during the prescription plan such that the assembly adjusting the least amount may always be assigned the primary role.

Alternatively, or in addition, the primary role assignment/re-assignment may be based on load(s) experienced by one or more assemblies 510. As discussed herein, the spatial frame 50 may be positioned in a variety of anatomic locations and/or at various orientations. The orientation of the spatial frame 500 may change during adjustment in accordance with the prescription plan. Anatomic forces acting upon the spatial frame 500 may also change during the prescription plan. As a result, assemblies 510 may not be loaded evenly. Each assembly 510 may experience different load schemes at any given time and/or the loading schemes of each assembly may change during the prescription plan. As such, the spatial frame 500 may be configured to measure and/or record current draw(s) that may be attributed to actuating each assembly 510. For example, each assembly 510 may be configured to measure, sense, and/or determine current draw associated with each adjustment performed by that assembly, and then transmit this information to the primary strut, external device(s), etc. for analysis and determination of whether primary role needs to be assigned/re-assigned. Algorithms within the assembly electronics and/or external devices communicating with the assemblies may compare the measured current draw(s) to actuate each assembly and assign the primary role to the assembly drawing the least amount of current for adjustments. Further, the primary role assignment/re-assignment may be based on at least one of the following: current draw(s) of the last adjustment of each assembly, current draw(s) of each assembly over a past period, determined expected future current draw(s) from each assembly since position(s) of the assemblies relative to patient's anatomy may be known, and/or any other factors and/or any combination thereof. In some examples, the spatial frame 500 may include one or more direct load measuring devices, such as, for example, force sensor(s), inertial measurement unit(s) (IMUs), etc. that may allow direct determinations of loading of each assembly 510. Since resistance to actuation for each assembly may be related to the load it is experiencing, the primary role may be assigned/re-assigned to the assembly which is loaded the least at the beginning of prescription plan, the assembly which is loaded the least at a predetermined time during prescription plan, and/or at any other time, and/or any combination thereof.

Alternatively, or in addition, assignment/re-assignment of primary role among assemblies 510 may be dependent on time (e.g., time intervals) to allow for managing of power drain on the primary assembly's power source. For instance, one or more assemblies 510 and/or one or more external devices may be programmed to assign/re-assign the primary role once during a particular time interval (e.g., hour, day, week, month, etc.). At a predetermined time during that time interval, the current subject matter may be configured to check the power levels of all power sources of assemblies 510 and assign/re-assign the primary role to the assembly that has the most power remaining in its power source. Moreover, the primary role may also be assigned/re-assigned after a predetermined number of adjustment cycles executed by the spatial frame 500 (as a whole) and/or one or more assemblies 510.

Alternatively, or in addition, sometimes it might be possible that it will not be technically feasible to determine which assembly 510 should be the primary assembly without one or more external devices (e.g., a smartphone, a computer, etc.) being used and connected to one or more assemblies 510. In this case, the primary assembly may be determined by the external device with which the external device may communicate. For some patients, e.g., pediatric patients, they may not be near the paired external device for hours at a time and as such, primary role may be assigned/re-assigned at the time of reconnection with the external device.

As can be understood, other factors may be used by the current subject matter to determine how, when and/or whether to assign/re-assign primary roles to/from one or more assemblies 510 in the spatial frame 500. The above are provided herein as illustrative examples only and are not intended to limit the current subject matter in any way. The current subject matter provides numerous advantages in optimizing battery life of assemblies in the spatial frame. For example, the current subject matter may be configured to reduce a burden of using an automated spatial frame for both surgeons and patients by absolving a need for a large non-rechargeable battery, which is cumbersome, heavy, interferes with fixation, and is difficult to replace. The current subject matter provides an easy and efficient way of managing and optimizing battery life to allow for a complete treatment for patients without a need for a battery change.

In accordance with one or more features of the present disclosure, motorization and/or automation of an existing manual strut is achieved in a significantly simpler manner thus reducing risk of failure. In various examples, the geared-motor assemblies eliminate the need for sterilization and offer a quick and simple method for implementing motorized and/or automated adjustment capability in a treatment plan. A companion APP can be used to transmit and receive commands and updates for the detachable geared-motor assemblies. For example, the companion APP can be configured to scan for beacons at set time intervals and establish connections with one or more of the geared-motor assemblies depending on whether a primary/secondary communication scheme is implemented. The connections enabling the receipt and/or transmission of data, updates, etc. The companion APP can be programmed to track a patient's treatment plan in terms of (a) force-feedback, (b) date and time of distraction, (c) lengthening schedule/direction, (d) rate (mm/day) and rhythm (steps/day) of distraction, (e) distraction length and (f) potential adverse events/complications.

While the present disclosure refers to certain examples, numerous modifications, alterations, and changes to the described examples are possible without departing from the sphere and scope of the present disclosure, as defined in the appended claim(s). Accordingly, it is intended that the present disclosure not be limited to the described examples, but that it has the full scope defined by the language of the following claims, and equivalents thereof. The discussion of any example is meant only to be explanatory and is not intended to suggest that the scope of the disclosure, including the claims, is limited to these examples. In other words, while illustrative examples of the disclosure have been described in detail herein, it is to be understood that the inventive concepts may be otherwise variously embodied and employed, and that the appended claims are intended to be construed to include such variations, except as limited by the prior art.

The foregoing discussion has been presented for purposes of illustration and description and is not intended to limit the disclosure to the form or forms disclosed herein. For example, various features of the disclosure are grouped together in one or more examples or configurations for the purpose of streamlining the disclosure. However, it should be understood that various features of the certain examples or configurations of the disclosure may be combined in alternate examples or configurations. Any example or feature of any section, portion, or any other component shown or particularly described in relation to various examples of similar sections, portions, or components herein may be interchangeably applied to any other similar example or feature shown or described herein. Additionally, components with the same name may be the same or different, and one of ordinary skill in the art would understand each component could be modified in a similar fashion or substituted to perform the same function.

Moreover, the following claims are hereby incorporated into this Detailed Description by this reference, with each claim standing on its own as a separate example of the present disclosure.

As used herein, an element or step recited in the singular and proceeded with the word "a" or "an" should be understood as not excluding plural elements or steps, unless such exclusion is explicitly recited. Furthermore, references to "one example" of the present disclosure are not intended to be interpreted as excluding the existence of additional examples that also incorporate the recited features.

The phrases "at least one", "one or more", and "and/or", as used herein, are open-ended expressions that are both conjunctive and disjunctive in operation. The terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. All rotational references describe relative movement between the various elements. Identification references (e.g., primary, secondary, first, second, third, fourth, etc.) are not intended to connote importance or priority but are used to distinguish one feature from another. The drawings are for purposes of illustration only and the dimensions, positions, order and relative to sizes reflected in the drawings attached hereto may vary.

The invention claimed is:

1. A spatial frame, comprising:

a first platform;

a second platform spaced from the first platform;

a plurality of adjustable length struts, each of the plurality of adjustable length struts coupled to the first platform and the second platform, each of the adjustable length struts including a housing and a threaded rod, wherein the threaded rod is arranged and configured to move relative to the housing to adjust a length of the strut; and a plurality of geared-motor assemblies, each of the plurality of geared-motor assemblies being arranged and configured to couple to one of the plurality of adjustable length struts, wherein each of the plurality of geared-motor assemblies is arranged and configured as a self-contained unit including electronics to (i) wirelessly communicate with an external computing device and (ii) to adjust the length of the strut to which it is coupled; and a power supply arranged and configured to provide power to the electronics;

wherein one of the plurality of geared-motor assemblies is configured as a primary assembly, the remaining plurality of geared-motor assemblies are configured as secondary assemblies, the primary assembly being arranged and configured to communicate with the external computing device to receive instructions and to transmit instructions to the secondary assemblies.

2. The spatial frame of claim 1, wherein each of the plurality of geared-motor assemblies is devoid of any external wires for coupling to an external controller.

3. The spatial frame of claim 1, wherein each of the geared-motor assemblies includes:

a housing;

a motor including an output shaft and a gear; and a printed-circuit board including a microprocessor and a wireless communication chip.

4. The spatial frame of claim 1, wherein the primary assembly is selectively interchangeable such that responsibilities associated with the primary assembly can be transferred to one of the secondary assemblies.

5. The spatial frame of claim 4, wherein responsibilities associated with the primary assembly are transferred to one of the secondary assemblies based on remaining power supply of the primary assembly.

6. The spatial frame of claim 5, wherein responsibilities associated with the primary assembly are transferred to one of the secondary assemblies when a remaining power supply level of the primary assembly is below a threshold value.

7. The spatial frame of claim 4, wherein responsibilities associated with the primary assembly are transferred to one of the secondary assemblies based on a predetermined schedule.

8. The spatial frame of claim 4, wherein responsibilities associated with the primary assembly are transferred to one of the secondary assemblies at a predetermined time.

9. The spatial frame of claim 4, wherein responsibilities associated with the primary assembly are transferred to one of the secondary assemblies based on at least data received by the primary assembly from at least one secondary assembly.

10. The spatial frame of claim 9, wherein the data includes at least one of the following: a power supply level of the at least one secondary assembly, a load level of the at least one secondary assembly, a frequency of adjustments performed by the at least one secondary assembly, a length of adjustments performed by the at least one secondary assembly, one or more positioning coordinates of the at least one secondary assembly, an angle of adjustments performed by the at least one secondary assembly, a direction of adjustments of the at least one secondary assembly, and any combination thereof.

11. The spatial frame of claim 4, wherein responsibilities associated with the primary assembly are transferred to one of the secondary assemblies based on at least one of: a load data of the primary assembly, a load data of at least one secondary assembly, a power supply level of the primary assembly, a power supply level of the at least one secondary assembly, and any combination thereof.

12. The spatial frame of claim 4, wherein responsibilities associated with the primary assembly are transferred to one of the secondary assemblies in accordance with a prescription plan determined for the spatial frame.

13. The spatial frame of claim 4, wherein responsibilities associated with the primary assembly are transferred to one of the secondary assemblies based on an instruction received from one or more external devices communicatively coupled to at least one of the primary assembly and at least one secondary assembly.

14. The spatial frame of claim 1, wherein each of the plurality of struts include a gear coupled to the threaded rod; and each of the plurality of geared-motor assemblies include a housing, a motor including an output shaft and a gear associated therewith, the gear of the motor arranged and configured to be operatively coupled to the gear of the strut.

15. The spatial frame of claim 14, wherein each of the geared-motor assemblies further includes one or more idler gears arranged and configured to engage the gear of the motor and the gear of the strut.

16. The spatial frame of claim 15, wherein the gear of the strut is at least partially contained within the housing of the strut, the housing of the strut including an opening for providing access to the gear, and the housing of the geared-motor assembly includes an opening to enable one of the gear of the motor and one of the one or more idler gears to extend therethrough.

17. A spatial frame, comprising:

a first platform;

a second platform spaced from the first platform;

a plurality of adjustable length struts, each of the plurality of adjustable length struts coupled to the first platform and the second platform, each of the adjustable length struts including a housing, a threaded rod, and a gear coupled to the threaded rod, wherein the threaded rod is arranged and configured to move relative to the housing to adjust a length of the strut; and a plurality of geared-motor assemblies, each of the plurality of geared-motor assemblies being arranged and configured to couple to one of the plurality of adjustable length struts, wherein each of the plurality of geared-motor assemblies is arranged and configured as a self-contained unit including:

a housing;

electronics to (i) wirelessly communicate with an external computing device and (ii) to adjust the length of the strut to which it is coupled;

a power supply arranged and configured to provide power to the electronics; and a motor including an output shaft and a gear associated therewith, the gear of the motor arranged and configured to be operatively coupled to the gear of the strut, wherein the housing of the strut includes an opening for providing access to the gear coupled to the threaded rod and at least partially contained within the housing of the strut, and the housing of the geared-motor assembly includes an opening to enable the gear of the motor, or one or more idler gears coupled thereto, to extend therethrough;

wherein the housing of the strut further includes a first recess and a peg recess; and the housing of the geared-motor assembly includes a first projection and a spring-loaded peg extending from a surface thereof, the first recess formed in the housing of the strut arranged and configured to receive the first projection of the geared-motor assembly.

18. The spatial frame of claim 17, wherein, with the first projection received within the first recess, the geared-motor assembly can be rotated relative to the strut.

19. The spatial frame of claim 18, wherein rotation of the geared-motor assembly relative to the strut causes the spring-loaded peg of the geared-motor assembly to be received within the peg recess.

20. The spatial frame of claim 19, wherein rotation of the geared-motor assembly relative to the strut causes the spring-loaded peg to contact a ramp formed on the housing of the strut to compress the spring-loaded peg until the spring-loaded peg is aligned with the peg recess.

21. The spatial frame of claim 19, wherein the housing of the strut further includes a second recess; and the housing of the geared-motor assembly includes a second projection extending from a surface thereof, the second recess formed in the housing of the strut arranged and configured to receive the second projection of the geared-motor assembly.

22. The spatial frame of claim 21, wherein rotation of the geared-motor assembly relative to the strut causes the second projection to be received within the second recess.

23. The spatial frame of claim 17, wherein the housing of the strut further includes a removal hole in communication with the peg recess so that a tool can be inserted to facilitate removal of the spring-loaded peg from the peg recess to enable the geared-motor assembly to be disengaged from the strut.

* * * * *